(12) United States Patent
Kim

(10) Patent No.: US 11,084,038 B2
(45) Date of Patent: Aug. 10, 2021

(54) PCR DEVICE HAVING UNIDIRECTIONAL SLIDING MEANS AND METHOD FOR PCR USING SAME

(71) Applicant: NANOBIOSYS INC., Seoul (KR)

(72) Inventor: Sung Woo Kim, Seoul (KR)

(73) Assignee: NANOBIOSYS INC., Seoul (KR)

( * ) Notice: Subject to any disclaimer, the term of this patent is extended or adjusted under 35 U.S.C. 154(b) by 242 days.

(21) Appl. No.: 15/116,386

(22) PCT Filed: Feb. 9, 2015

(86) PCT No.: PCT/KR2015/001291
§ 371 (c)(1),
(2) Date: Aug. 3, 2016

(87) PCT Pub. No.: WO2015/119470
PCT Pub. Date: Aug. 13, 2015

(65) Prior Publication Data
US 2017/0008000 A1    Jan. 12, 2017

(30) Foreign Application Priority Data

Feb. 10, 2014    (KR) .................. 10-2014-0014777

(51) Int. Cl.
*B01L 7/00*    (2006.01)
*C12Q 1/6844*    (2018.01)

(52) U.S. Cl.
CPC ............. *B01L 7/525* (2013.01); *B01L 7/5255* (2013.01); *C12Q 1/6846* (2013.01);
(Continued)

(58) Field of Classification Search
CPC .. B01L 7/525; B01L 7/5255; B01L 2300/045; B01L 2300/12; B01L 2300/087;
(Continued)

(56) References Cited

U.S. PATENT DOCUMENTS 5,736,106 A * 4/1998 Ishiguro .................... B01L 7/52
165/133
5,819,842 A    10/1998 Potter
(Continued)

FOREIGN PATENT DOCUMENTS

CN    101711257 A    5/2010
CN    102985527 A    3/2013
(Continued)

OTHER PUBLICATIONS

Baek Seung Yeb, "English language machine translation." (Year: 2006).*

(Continued)

*Primary Examiner* — Liban M Hassan
(74) *Attorney, Agent, or Firm* — Novick, Kim & Lee, PLLC; Sang Ho Lee

(57) ABSTRACT

Described is a polymerase chain reaction (PCR) device including a PCR thermal block including a first substrate and heating units, a PCR chip including a second substrate and reaction chambers, and an unidirectional sliding driver for sliding the PCR chip relative to the PCR thermal block while maintaining a contact between the second substrate of the PCR chip and the first substrate of the PCR thermal block. The first and second heaters of each of the plurality of heating units are spaced apart from each other along a sliding direction, and the unidirectional sliding driver causes any reaction chamber in the PCR chip to have a sequential thermal contact from a heater of the plurality of heating units mounted at one end of the PCR thermal block to a heater of the plurality of heating units mounted at another end of the PCR thermal block.

19 Claims, 15 Drawing Sheets

(52) U.S. Cl.
CPC .... *B01L 2200/025* (2013.01); *B01L 2300/045* (2013.01); *B01L 2300/0627* (2013.01); *B01L 2300/0645* (2013.01); *B01L 2300/0654* (2013.01); *B01L 2300/087* (2013.01); *B01L 2300/0816* (2013.01); *B01L 2300/0819* (2013.01); *B01L 2300/0829* (2013.01); *B01L 2300/12* (2013.01); *B01L 2300/1822* (2013.01); *B01L 2300/1827* (2013.01)

(58) Field of Classification Search
CPC ..... B01L 2300/0816; B01L 2300/0627; B01L 2200/025; B01L 2300/1822; B01L 2300/0645; B01L 2300/0819; B01L 2300/1827; B01L 2300/0654; B01L 2300/0829; C12Q 1/6846
USPC ..................................................... 435/287.2
See application file for complete search history.

(56) References Cited

U.S. PATENT DOCUMENTS

| | | | | |
|---|---|---|---|---|
| 6,533,255 | B1* | 3/2003 | Mitsuhashi | ............... B01L 7/02 261/149 |
| 6,572,828 | B1* | 6/2003 | Potyrailo | ................. B01L 7/52 422/129 |
| 2001/0041357 | A1* | 11/2001 | Fouillet | ............ B01L 3/502784 435/91.1 |
| 2005/0026277 | A1 | 2/2005 | Festoc | |
| 2007/0098600 | A1* | 5/2007 | Kayyem | ............... B01L 3/5027 422/400 |
| 2010/0173794 | A1 | 7/2010 | Vossenaar | |
| 2011/0129914 | A1 | 6/2011 | Schlaubitz | |
| 2012/0295312 | A1 | 11/2012 | Seo et al. | |
| 2012/0322064 | A1* | 12/2012 | Alocilja | ................. B82Y 15/00 435/6.11 |
| 2013/0040377 | A1* | 2/2013 | Kim | ....................... C12Q 1/686 435/287.2 |

FOREIGN PATENT DOCUMENTS

| | | |
|---|---|---|
| EP | 0545736 A | 6/1993 |
| EP | 2562247 A2 | 2/2013 |
| JP | H09-510863 A | 11/1997 |
| KR | 10-2006-0116984 A | 11/2006 |
| KR | 10-2011-0118572 A | 10/2011 |
| KR | 10-2012-0137054 A | 12/2012 |
| KR | 10-2012-0139205 A | 12/2012 |
| RU | 2385940 C1 | 4/2010 |
| WO | 2008/091626 A1 | 7/2008 |
| WO | 2011/132977 A2 | 10/2011 |
| WO | 2014/017821 A1 | 1/2014 |

OTHER PUBLICATIONS

Kim et al., "English language machine translation." (Year: 2012).*
T. H. Fang et al., "Real-time PCR microfluidic devices with concurrent electrochemical detection" Abstract, Biosensors and Bioelectronics, vol. 24, Issue 7, pp. 2131-2136 (Mar. 15, 2009).

* cited by examiner

_PCR DEVICE HAVING UNIDIRECTIONAL SLIDING MEANS AND METHOD FOR PCR USING SAME_

TECHNICAL FIELD

The present invention relates to a PCR device, which includes a PCR thermal block having heaters arranged continuously and repeatedly and a PCR chip having reaction chambers arranged repeatedly, and a method for PCR using the same.

BACKGROUND ART

Polymerase chain reaction (hereinafter, called 'PCR') is a technology that sequentially copies a specific region of template nucleic acids by repeatedly heating and cooling the specific region in order to amplify the nucleic acids having the specific region in geometrical progression, and has been widely used in genetic engineering, medical fields, and so on for purposes of analysis and diagnosis. Recently, various devices for effectively executing PCR have been developed.

A conventional PCR device comprises: a tube type reaction container into which a sample solution containing template nucleic acids are injected and mounted in a single heater. The reaction container is repeatedly heated and cooled to execute PCR (see FIGS. 1 and 2). Such a PCR device has advantages in that it is not complicated in structure because having just one heater can increase the density of samples simply because a plurality of samples can be induced. However, such a PCR device has several disadvantages in that it must have a complicated circuit in order to accurately control temperature, it needs many samples because the tube type reaction container is large in size, and the entire PCR time increases due to the repeated heating and cooling of a single heater.

Moreover, according to another conventional PCR device, a plurality of heaters having different PCR temperatures are mounted, and PCR is executed in such a way that a sample solution having nucleic acids flows through one flow channel to pass through the heaters (see FIG. 3). This PCR device has an advantage in that PCR time is short as the presence of many heaters with different PCR temperatures reduces the need to repeatedly heat and cool the heaters. However, such a PCR device has several disadvantages in that it can implement a relatively simple circuit as using the plural heaters but it is complicated in the entirety of the structure as it requires a long flow channel to pass through the high-temperature heaters and the low-temperature heaters; is difficult to apply a plurality of samples; and it requires a separate control unit to control the flow of the sample solution having nucleic acids flowing inside the flow channel passing through the heaters so that it is difficult to increase density of the sample and the device.

Recently, effective methods have been proposed for improving PCR devices and methods that are capable of increasing PCR yield and recognizing PCR process in real time, treating many samples in one PCR process by increasing density, and also increasing throughput of the samples by reducing PCR time. In this instance, technology for accurately controlling and setting temperature of the heaters arranged in a row without needing repeated heating and cooling, technology to transfer lots of samples so that PCR can be executed to the samples at the same time using the heaters at the setting temperature, and a PCR device using the above-mentioned technology are still in demand.

INVENTION

Technical Problem

Accordingly, the present invention has been made in an effort to solve the above-mentioned problems occurring in the prior arts, and it is an object of the present invention to provide a PCR device capable of considerably enhancing PCR time, PCR yield, and a throughput of samples measured and analyzed in real time.

Technical Solution

To achieve the above objects, the present invention provides a PCR device including: PCR thermal blocks having two or more heaters repeatedly arranged on an upper surface of a substrate to be spaced apart from each other; a plate type PCR chip having two or more reaction chambers repeatedly mounted in such a way as to meet the two or more heaters arranged on the PCR thermal blocks when getting in contact with the PCR thermal blocks; and unidirectional sliding means which serves to slid while maintaining the contact between the PCR chip and the PCR thermal blocks in the state where the PCR chip is mounted, the unidirectional sliding means being formed to cause a sequential thermal contact between the two or more reaction chamber repeatedly arranged from one end of the PCR chip to the other end and the two or more heaters repeatedly arranged from one end of the PCR thermal block to the other end during the sliding.

In one embodiment of the present invention, the neighboring heaters of the two or more heaters are different from each other in temperature.

The two or more heaters are formed in such a way that the first circulation of the PCR is carried out in the heater located at one end of the PCR thermal block and the final circulation is ended in the heater located at the other end of the PCR thermal block.

The two or more reaction chambers of the PCR chip are arranged and spaced apart from each other in a sliding direction of the PCR chip or in a vertical direction to the sliding direction, or are formed in a channel type to continuously pass in the vertical direction to the sliding direction of the PCR chip.

The reaction chamber of the PCR chip is formed in an integrated inlet/outlet well type or in a separate inlet/outlet channel type.

The PCR device further includes: a light source for supplying light to the reaction chambers of the PCR chip; and a light detector arranged to receive light emitted from a PCR reaction part.

The light source or the light detector are repeatedly arranged in spaces between the neighboring heaters of the PCR heating block, and move in correspondence to the movement route of the PCR chip.

The PCR chip includes a detection electrode for detecting electrochemical signals generated by combining amplified nucleic acids to a redox indicator in the reaction chamber. The PCR device further includes an electrochemical signal measuring module electrically connected to the detection electrode to measure the electrochemical signals generated from the interior of the reaction chamber of the PCR chip in real time.

The PCR chip includes: an immobilization layer formed on one region of the interior of the reaction chamber and subjected to surface treatment with a capture probe capable of being complementarily bonded to one region of the amplified target nucleic acids; a detection electrode formed on the other region of the reaction chamber so as to detect the electrochemical signals; and composites having metal nanoparticles and signaling probes connected to the metal nanoparticles in such a manner as to be complementarily bonded to the other region of the amplified target nucleic acids. Additionally, the PCR device further includes an electrochemical signal measuring module electrically connected to the detection electrode to measure the electrochemical signals generated from the interior of the reaction chamber of the PCR reaction unit.

The PCR device further includes a chip standby part which accommodates a plurality of PCR chips therein and in which the PCR chips are connected drivably in such a way that the first PCR chip sequentially conducts thermal contact with the PCR thermal blocks, and then, the second PCR chip starts to conduct thermal contact with the PCR thermal blocks.

Advantageous Effects

According to one embodiment of the present invention, the PCR device can rapidly and accurately execute PCR due to heating block having the heaters repeatedly arranged thereon is capable of preventing the radial thermal distribution generated from the individual heaters and the non-uniform heat superposition between the neighboring heaters to improve PCR yield and further capable of sparing separate temperature controlling means to achieve the miniaturization and integration of the device. Furthermore, the PCR device is capable of amplifying a plurality of nucleic acids samples at the same time and rapidly by using the PCR heating block on which the heater units are repeatedly arranged and the plate-shaped PCR reaction unit and also capable of measuring successively generated optical signals or electrochemical signals to check the process of nucleic acids amplification in real time.

MODE FOR INVENTION

Hereinafter, embodiments according to the present invention will be described in detail with reference to the attached figures. Explanation below is merely exemplary of the embodiments according to the present invention for easier understanding and it does not be meant to limit the protection scope thereto.

According to the embodiment of the present invention, PCR (Polymerase Chain Reaction) refers to a type of reaction for amplifying nucleic acids having specific sequence. So as to amplifying DNA (deoxyribonucleic acids) having specific sequence, for example, a PCR device conducts a denaturing step that a solution containing a PCR sample in which double-stranded DNA as template nucleic acids are contained and a reagent is heated to a given temperature, for example, about 95° C. and the double-stranded DNA is separated to single-stranded DNA, an annealing step that an oligonucleotide primer having a complementary sequence to the sequence of the DNA to be amplified is provided and cooled to a given temperature, for example, 55° C., together with the separated single-stranded DNA, and the primer is then bonded to the specific sequence of the single-stranded DNA to form a partial DNA-primer composite, and an extension (amplification) step that the solution is maintained to an appropriate temperature, for example, 72° C. after the annealing step and double-stranded DNA is formed on the basis of the primer of the partial DNA-primer composite by means of DNA polymerase. In this case, the three steps are repeatedly conducted 20 to 40 times to allow the DNA having the specific sequence to be amplified exponentially. In some cases, the PCR device conducts the annealing step and the extension (or amplification) step, at the same time, and at this time, the PCR device conducts two steps including the denaturing step and the annealing and extension step, thus finishing a first cycle. Accordingly, a PCR heating block and a PCR device having the same according to the embodiment of the present invention includes modules with which the above-mentioned steps are conducted. It is assumed that detailed modules not described herein have been disclosed in conventional technologies for the PCR or provided herein within the obvious scope of the present invention.

Figure 1:
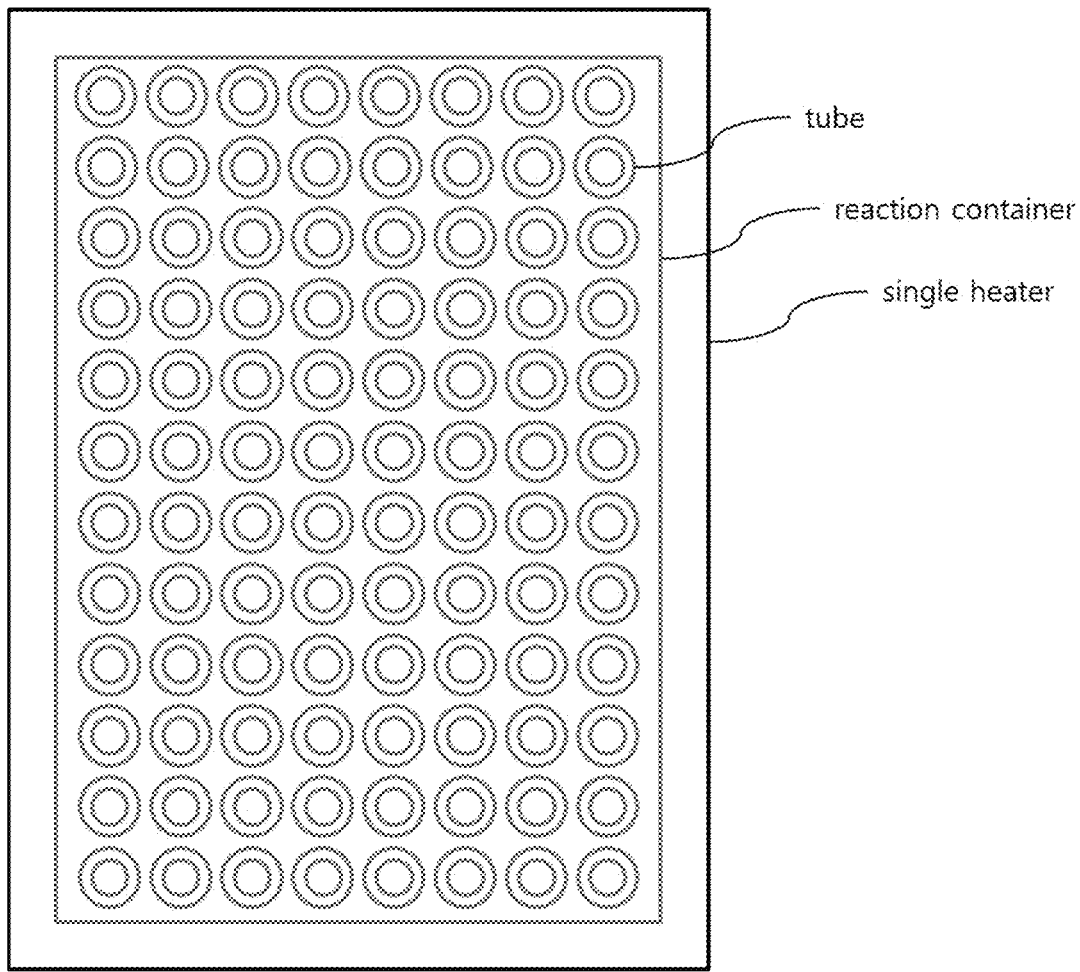
FIG. 1 is a plan view of a conventional PCR thermal block having a single heater and a PCR reaction container of a tube type mounted to the PCR thermal block.
Figure 2:
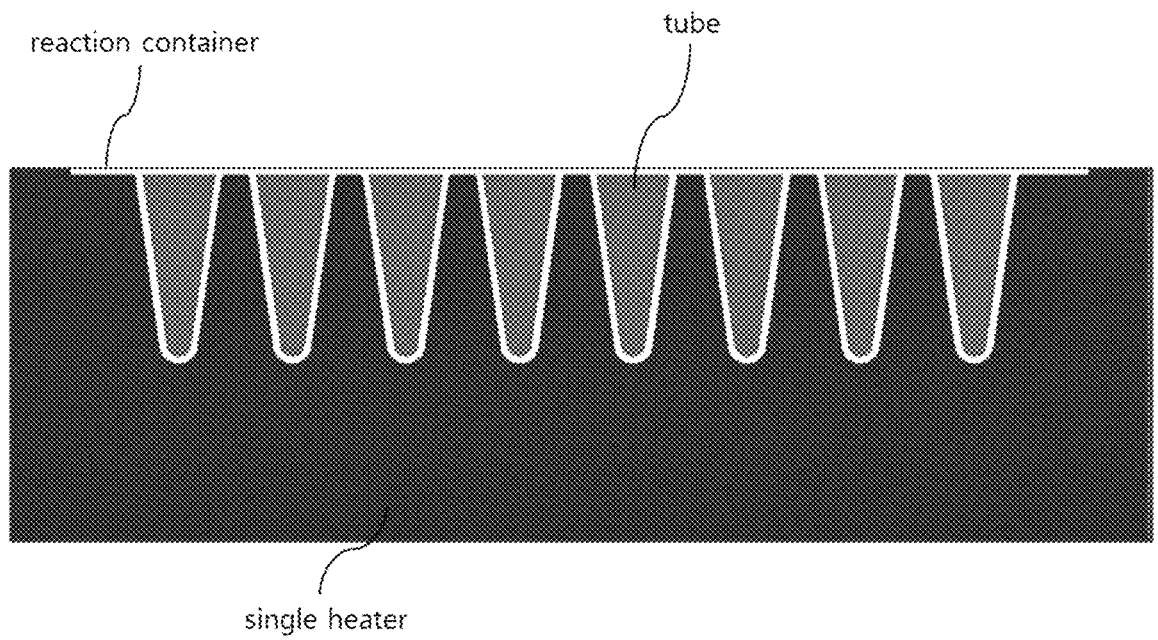
FIG. 2 is a side sectional view of the conventional PCR thermal block and the PCR reaction chamber.
Figure 3:
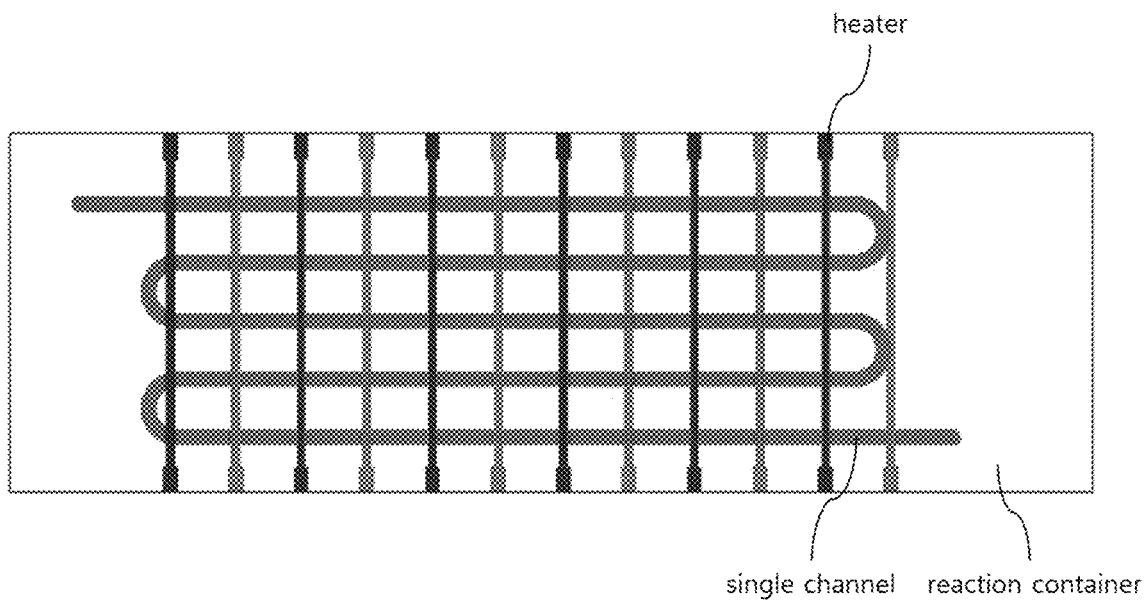
FIG. 3 is a plan view of a conventional PCR thermal block having a plurality of heaters and a PCR reaction container of a flow channel type mounted to the PCR thermal block.
Figure 4:
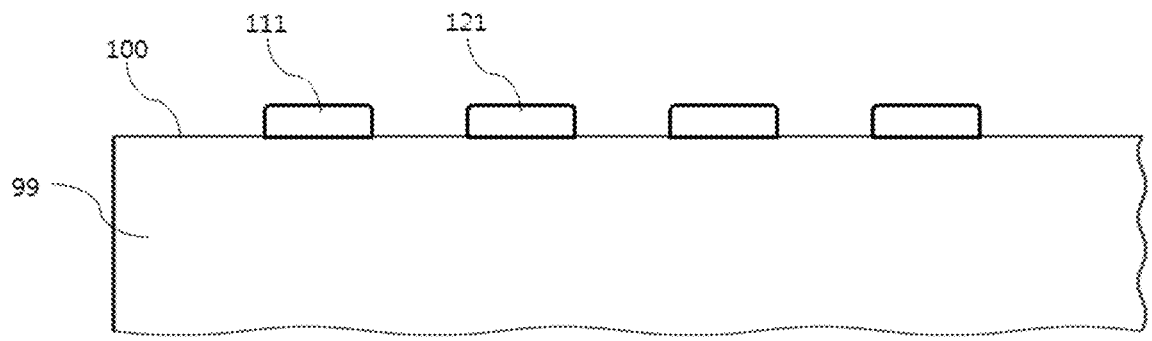
FIG. 4 is a PCR thermal block 100 having at least two heaters 111 and 121 which are repeatedly arranged on an upper face of a substrate 99 to be spaced apart from each other according to a preferred embodiment of the present invention.

FIG. 4 is a PCR thermal block 100 having at least two heaters 111 and 121 which are repeatedly arranged on an upper face of a substrate 99 to be spaced apart from each other according to a preferred embodiment of the present invention.

Referring to FIG. 4, the thermal block 100 according to the preferred embodiment of the present invention includes at least two heaters 111 and 121 which are repeatedly arranged on the upper surface of the PCR thermal block in order to supply heat to a PCR solution. The PCR thermal block 100 is a module for maintaining specific temperature, and includes a contact surface with a PCR reaction area on at least one surface so that heat is supplied to the PCR solution, namely, a sample and a reagent for conducting the PCR, through the thermal contact so as to conduct the PCR. A substrate 99 does not change in physical or chemical properties due to the heating of the heaters 111 and 121 arranged on the surface thereof and is made of a material which does not cause heat exchange between two or more heaters. For example, substrate 99 is made of a material like plastic, glass and silicone, and if necessary, it may be transparent or translucent. To achieve miniaturization and integration of a device, the PCR heating block 100 is formed of a generally thin plate having a thickness in the range of about 50 nm to 1 mm, and preferably, a thickness of about 250 μm. However, the thickness of the PCR heating block 100 is not limited thereto.

The two or more heaters are repeatedly arranged on the upper surface of the PCR heating block 100 to be spaced apart from each other, and for example, the two or more heaters of the PCR heating block 100 are formed in such a way that the first circulation of the PCR is carried out in the heater located at one end of the PCR thermal block and the final circulation is ended in the heater located at the other end of the PCR thermal block. Further, the PCR heating block 100 has various shapes for effectively supplying heat to the PCR reaction area, for instance, various shapes like a plane, channel, or pillar capable of increasing the surface to volume ratio.

The heaters 111 and 121 are conductive heating elements arranged on the substrate 99 and may be formed of heaters using Joule heating or thermoelements causing the Peltier effect. In the meantime, the neighboring heaters of the two or more heaters of the PCR thermal block 100 may have a different temperature, and a temperature pattern between the neighboring heaters may be repeated by combination of the predetermined number of the heaters. For instance, a first heater is at 95° C., a second heater is at 55° C. and a third heater is at 72° C., and such a temperature pattern may be repeated ten times, twenty times, thirty times or forty times. Alternatively, the first heater is at 95° C., the second heater is at 72° C. and a third heater is at 72° C., and such a temperature pattern may be repeated ten times, twenty times, thirty times or forty times. Therefore, the two or more heaters of the PCR heating block 100 are formed in such a way that the first circulation of the PCR is carried out in the heater (95° C.) located at one end of the PCR thermal block and the final circulation is ended in the heater (72° C.) located at the other end of the PCR thermal block.

The heaters 111 and 121 are operably connected to various power modules and control modules in order to maintain given temperatures and are also operably connected to sensors monitoring the temperatures of the heaters. So as to allow the internal temperatures of the heaters 111 and 121 to be constantly maintained, unit electrodes, that is, heater electrodes are symmetrically arranged in up and down and/or left and right directions around the center points of the surfaces of the heaters. So as to achieve rapid heat transmission and high conductivity, further, the heaters 111 and 121 are made of one or more materials selected from the group consisting of chrome, aluminum, copper, iron, silver and carbon, or made of their composite materials. However, the materials of the heaters are not limited thereto. Furthermore, the heaters 111 and 121 may include one or more materials selected from the group consisting of conductive nanoparticles containing light transmission heating elements, for example, an oxide semiconductor and a material to which impurities selected from the group consisting of In, Sb, Al, Ga, C and Sn are added to the oxide semiconductor, indium tin oxide, conductive polymer, carbon nanotube and graphene.

In the case that the two heaters 111 and 121 are arranged on the PCR heating block 100 twice to execute two steps for the PCR, that is, the denaturing step and the annealing/extension step, the PCR time is shorter than that required for the three steps including the denaturing step, the annealing step and the extension step. Furthermore, since the number of heaters is reduced, it has advantages enhancing the simplification and integrity of the structure. In the three steps for PCR, on the other hand, the temperature of the denaturing step is in the range of 85 to 105° C., preferably 95° C., the temperature of the annealing step is in the range of 40 to 60° C., preferably 50° C., and the temperature of the extension step is in the range of 50 to 80° C., preferably 72° C. In the two steps for PCR, furthermore, the temperature of the denaturing step is in the range of 85 to 105° C., preferably 95° C., and the temperature of the annealing/extension step is in the range of 50 to 80° C., preferably 72° C. However, the given temperatures and the ranges of the given temperatures for the PCR may be of course adjustable in the range known.

As described above, the two or more heaters 111 and 121 maintaining the given temperatures are repeatedly arranged on the upper surface of the PCR heating block 100 to be spaced apart from each other, thus substantially increasing the temperature to time ratio. According to the conventional device where a single heater is disposed, for example, the temperature to time ratio is in the range of 3 to 7° C. per second. However, according to the embodiment of the present invention having repeatedly arranged heater structure, the temperature to time ratio between the heaters is in the range of 20 to 40° C. per second, thus reducing the time for PCR. According to the embodiment of the present invention having repeatedly arranged heater structure, the temperatures at the denaturing step, the annealing step and the extension step (or the denaturing step and the annealing/extension step) can be accurately controlled, and further, it is possible to maintain desired temperatures or temperature ranges only at portions at which heat is supplied from the heaters. Also, a various number of the heater units 10 and 20 are repeatedly arranged on the PCR heating block 100, thus achieving various PCR cycle times. For example, in case of the PCR having 10 cycles, the 20 or 30 heaters are repeatedly arranged. That is, the heater units may be repeatedly arranged e.g., 10 times, 20 times, 30 times, 40 times, or 50 times on the PCR heating block 100 according to intended PCR cycles.

Figure 5:
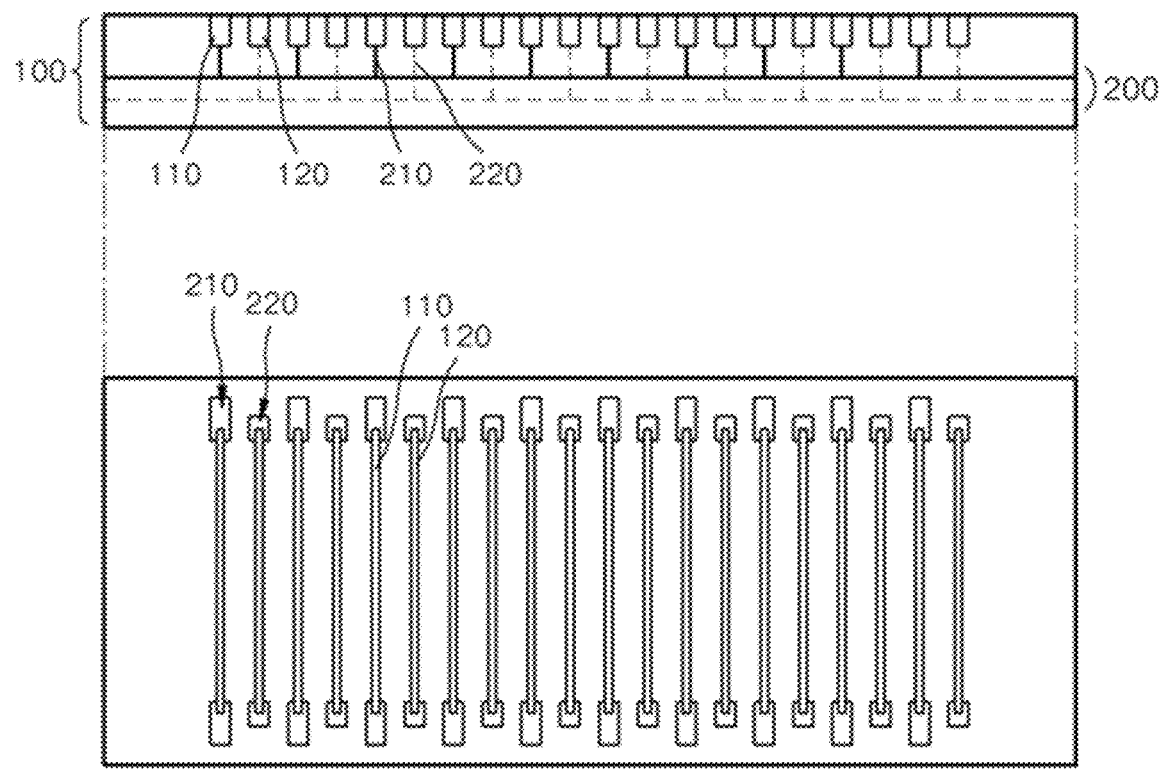
FIG. 5 is a view showing an arrangement structure of heaters of the PCR thermal block 100 according to the preferred embodiment of the present invention.

FIG. 5 shows the PCR heating block 100 according to the present invention and a power supply part 200 supplying power to the heaters repeatedly arranged on the PCR heating block 100. In more detail, the upper end portion of FIG. 5 shows a vertical sectional view of the PCR heating block 100, and the lower end portion of FIG. 5 shows a plan view of the PCR heating block 100. Referring to FIG. 5, the PCR heating block 100 includes 20 heaters repeatedly arranged. The power supply part 200 is a module supplying power to the PCR heating block 100 from a power supply source so as to heat the PCR heating block 100 and includes first and second distributed wires 210 and 220 adapted to distribute power to the heaters 110 and 120. Referring to FIG. 5, for example, a first distributed wire 210 of the PCR heating block 100 is located to supply power to the first heaters 110, and a second distributed wire 220 of the PCR heating block 100 is located to supply power to the second heaters 120. If the first heaters 110 maintain a temperature of the PCR denaturing step, for example, a temperature of 85 to 105° C. and the second heaters 120 maintains a temperature of the PCR annealing/extension step, for example, a temperature of 50 to 80° C., the first distributed wire 210 receives the power for maintaining the temperature of the PCR denaturing step from the power supply part 200 and the second distributed wire 220 receives the power for maintaining the temperature of the PCR annealing/extension step from the power supply part 200. The first distributed wire 210 and the second distributed wire 220 are made of a conductive material like gold, silver, copper and so on, but they are not limited thereto. The power supply source is a module supplying power to the power supply part 200 and is connected correspondingly to the first distributed wire 210 and the second distributed wire 220 of the power supply part 200. While the PCR is being conducted, for example, a first power port of the power supply sources 400 is electrically connected to the first distributed wire 210, and a second power port of the power supply sources 400 is electrically connected to the second distributed wire 220. After that, if a command for conducting the PCR is issued from a user, the power supply source supplies power to the first distributed wire 210 and the second distributed wire 220 and rapidly heats the first heater and the second heater of the PCR heating block 100. If the heaters reach given temperatures, further, the power supply source controls the quantity of power supplied to allow the heaters to maintain the given temperatures.

Figure 6:
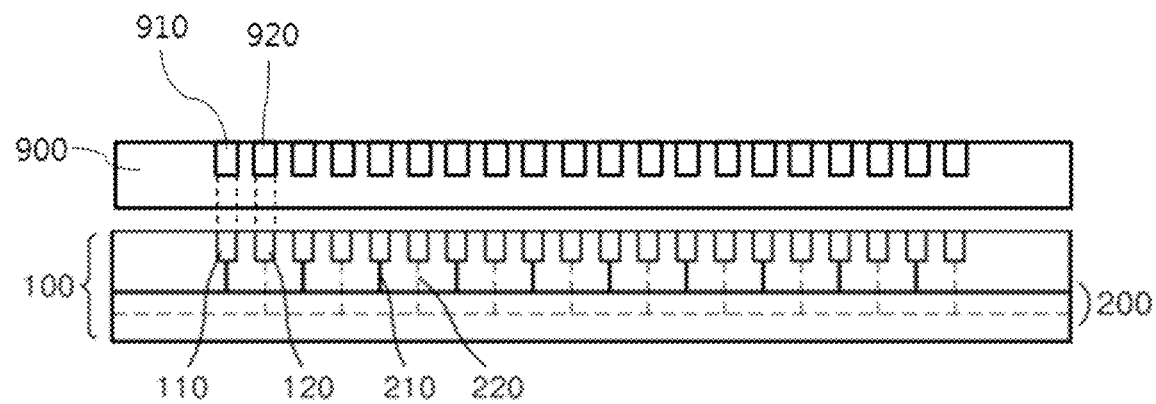
FIG. 6 is a view showing an arrangement structure of a PCR chip 900 and at least two reaction chambers 910 arranged inside the PCR chip according to the preferred embodiment of the present invention.
Figure 7:
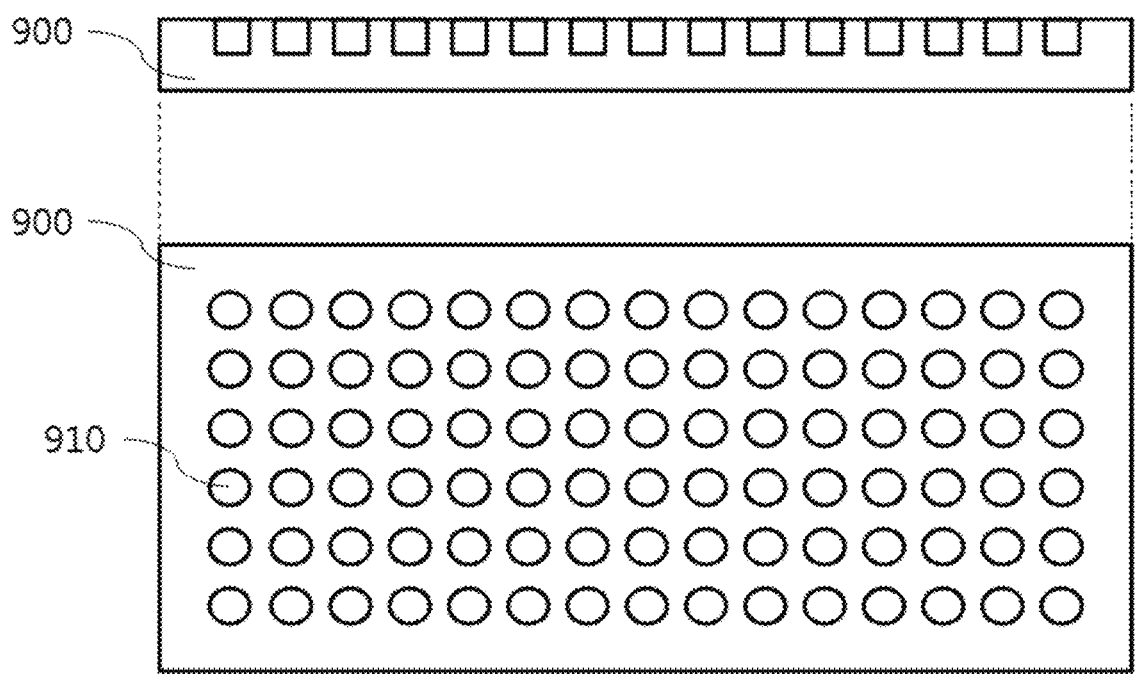
FIGS. 7 to 9 are views showing PCR chips 900 of various types according to the preferred embodiment of the present invention.
Figure 8:
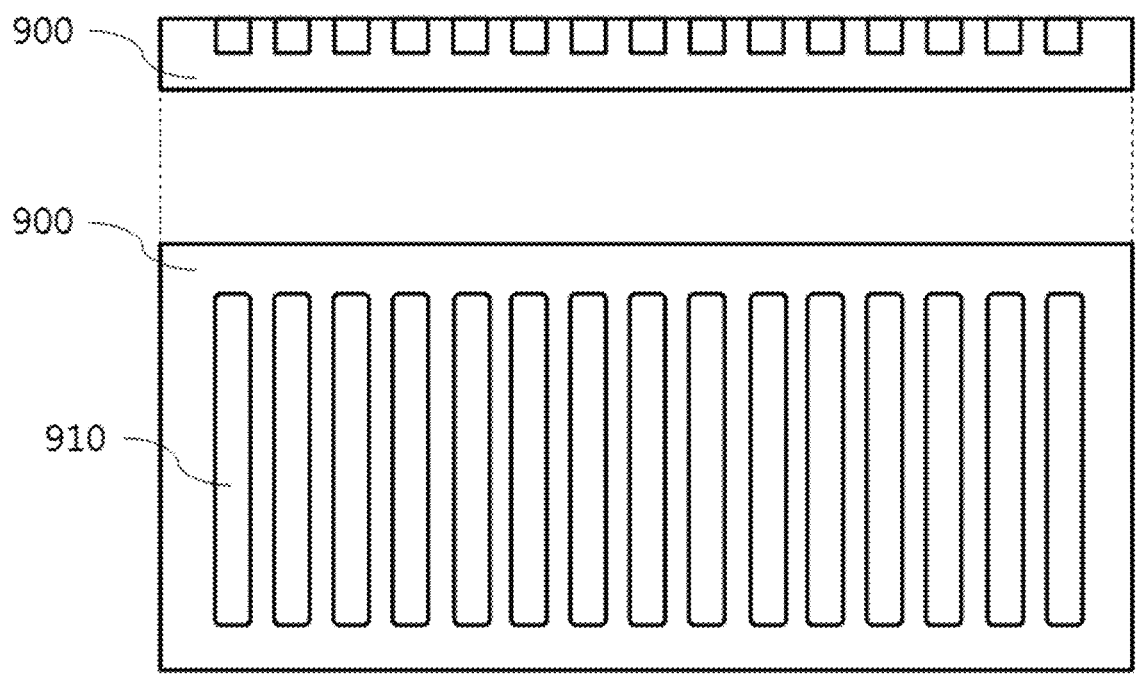
Figure 9:
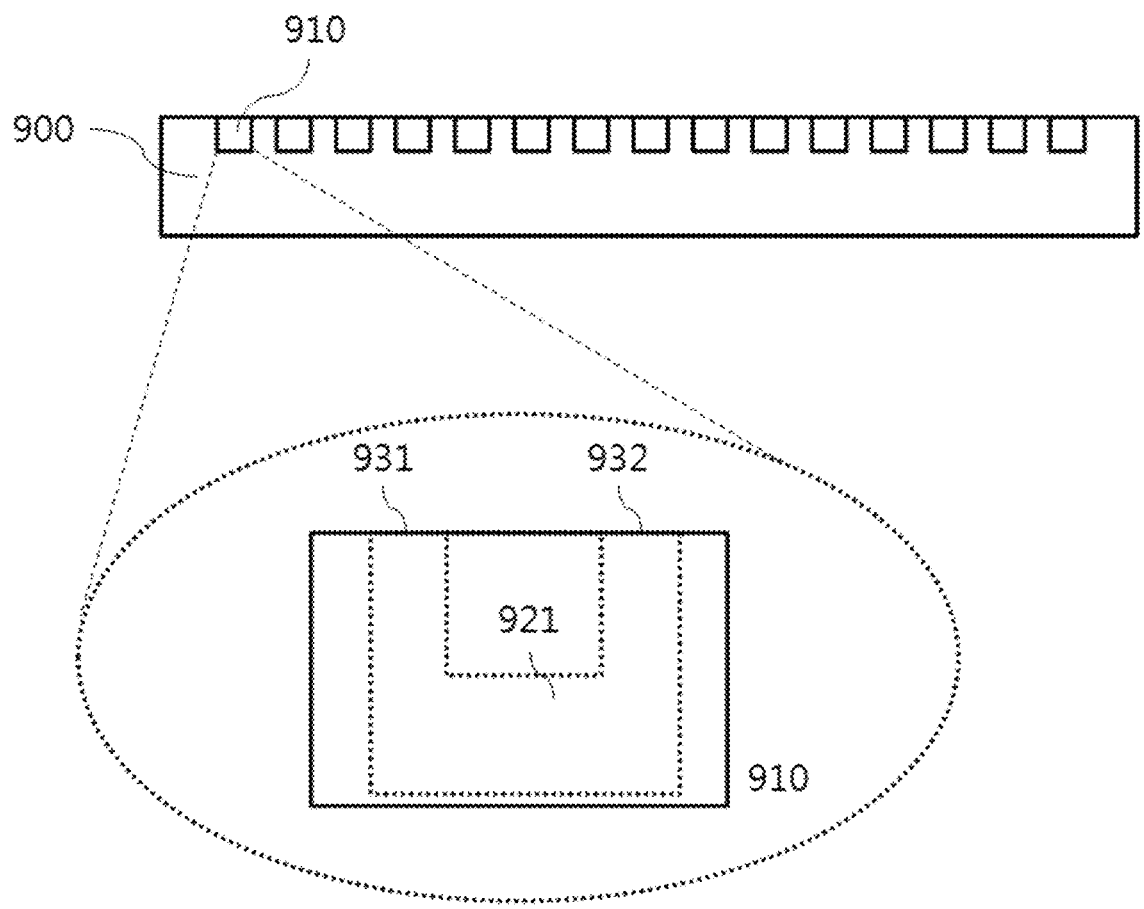

FIG. 6 is a view showing an arrangement structure of a PCR chip 900 and at least two reaction chambers 910 arranged inside the PCR chip according to the preferred embodiment of the present invention, and FIGS. 7 to 9 are views showing PCR chips 900 of various types according to the preferred embodiment of the present invention.

Referring to FIG. 6, the PCR chip 900 according to the preferred embodiment of the present invention is in the form of a plate, gets in contact with the upper surface of the PCR thermal block 100, in detail, with the heaters 110 and 120, and includes two or more reaction chambers 910 and 920 repeatedly arranged to meet the two or more heaters 110 and 120 arranged on the PCR thermal block 100 when getting in contact. Based on this premise, FIGS. 7 to 9 illustrate PCR chips 900 of various types according to the preferred embodiment of the present invention.

The reaction chamber is a space for accommodating a solution containing a PCR sample in which double-stranded DNA as template nucleic acids are contained and a reagent in order to amplify DNA (deoxyribonucleic acids) having specific sequence. In the embodiment of the present invention, the reaction chamber is arranged in a heater area disposed in the PCR thermal block 100 when coming into thermal contact with the PCR thermal block 100 to execute the PCR. In the meantime, the PCR chip is generally formed in a plate shape so that heat is evenly transferred to the reaction chambers when the PCR chip comes into thermal contact with the PCR thermal block 100.

Referring to FIG. 7, at least two reaction chambers 910 are repeatedly arranged on the plate-shaped chip. Moreover, the reaction chambers 910 may be arranged in a longitudinal direction of the chip or in a vertical direction to the longitudinal direction. In this instance, the reaction chambers 910 may contain the same or different PCR sample and reagent, and in this instance, the PCR having at least two or various kinds of samples is carried out through one PCR chip 900.

Referring to FIG. 8, two or more reaction chambers 910 of a plate shape are arranged repeatedly, and may be formed in a channel type which continuously passes in the vertical direction to the longitudinal direction of the chip. In this instance, the reaction chambers 910 may contain the same or different PCR sample and reagent, and in this instance, the PCR having at least two or various kinds of samples is carried out through one PCR chip 900.

Meanwhile, the reaction chamber 910 of the PCR chip 900 shown in FIGS. 7 and 8 is formed in an integrated inlet and outlet well type in which an inlet and an outlet are integrated into one. However, the reaction chamber 910 of the PCR chip 900 shown in FIG. 9 is formed in a separate inlet and outlet channel type in which an inlet 931 and an outlet 932 are formed separately and are connected to each other through a single channel 921. A conventional PCR chip of a multi well plate type is low in a surface to volume ratio and requires long PCR time because the volume of samples is large. However, the PCR chip of the separate inlet and outlet channel type according to the preferred embodiment of the present invention is high in the surface to volume ratio, thereby considerably reducing PCR time. The height of the channel inside the reaction chamber may be selected in a range of 0.01 μm to 5 mm, but it is preferable that the height of the channel gets lower so that the surface to volume ratio gets higher.

In the meantime, the PCR chip 900 according to the preferred embodiment of the present invention includes: a first plate getting in contact with the PCR thermal block 100; a second plate which is arranged on the first plate and has two or more reaction chambers; and a third plate which is arranged on the second plate and has an inlet and an outlet for the two or more reaction chambers. As described above, the PCR chip 900 has a plate type laminated structure, thus providing a simple manufacturing process and a low manufacturing cost and widening a heat exchange area with the PCR thermal block 100. The PCR chip 900 may be made of various materials, and preferably, it is made of a plastic thin film. Further, the PCR chip 900 is made of a light transmissive material, and if it is used for real time PCR based on optical measurements like fluorescence, phosphorescence, luminescence, Raman spectroscopy, surface enhanced Raman scattering and surface Plasmon resonance, the PCR reaction unit 300 is preferably made of a light transmissive material.

The first plate is bonded or attached to the PCR thermal block 100 and receives heat from the PCR thermal block 100. The first plate is made of various materials, and preferably, is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, hydrophilic substance (not shown) is treated to the top surface of the first plate 310 so as to serve to gently conduct the PCR. Through the treatment of the hydrophilic substance, accordingly, a single layer containing the hydrophilic substance is formed on the first plate 310. The hydrophilic substance includes various materials, and preferably, includes a material selected from the group consisting of carboxyl group (—COOH), amine group (—NH2), hydroxyl group (—OH), and sulfone group (—SH). The treatment of the hydrophilic substance is conducted in a manner known in the art.

The second plate is disposed on top of the first plate 310. The second plate has two or more reaction chambers. Accordingly, a target sample solution to be amplified is introduced into the two or more reaction chambers, and then, the PCR is conducted. Further, the second plate 320 is made of various materials, and preferably, it is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. Additionally, the second plate has various thicknesses, and preferably, it has a thickness of 0.01 µm to 5 mm. The reaction chambers have various widths and lengths, and preferably, have a width of 0.001 mm to 10 mm and a length of 1 mm to 400 mm. Furthermore, the inner wall of the second plate is coated with a material like silane group, bovine serum albumin (BSA) and so on, so as to prevent protein from being absorbed thereto. The treatment of the material is conducted in a manner known in the art.

The third plate is disposed on the top of the second plate. The third plate has an inlet formed on one area thereof on each reaction chamber formed on the second plate and an outlet formed on the other area thereof on each reaction chamber. The inlet is a portion into which the target sample solution containing the nucleic acids nucleic acids to be amplified is introduced. The outlet is a portion through which the target sample solution is discharged after the completion of the PCR. As described above, the inlet and the outlet may be formed in the integrated type or the separate type, and the inner surfaces of the inlet and the outlet are consecutively connected with the inner surfaces of the two or more reaction chambers of the second plate. In the meantime, the third plate is made of various materials, and preferably, is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, the inlet has various sizes, and preferably, it has a diameter of 0.001 to 10 mm. Furthermore, the outlet has various sizes, and preferably, it has a diameter of 0.001 to 10 mm. In addition, covering means are mounted on the inlet and the outlet so as to prevent the target sample solution in the two or more reaction chambers from leaking when the PCR for the target sample solution is conducted. The covering means have various shapes, sizes or materials. In addition, the third plate has various thicknesses, and preferably, it has a thickness of 0.001 to 10 mm.

The PCR chip 900 is easily manufactured through a method including the steps of: providing the third plate having the inlet and the outlet formed by means of machining; forming two or more reaction chambers at portions corresponding to the inlet and the outlet of the third plate on a plate having the corresponding size to the underside surface of the third plate by means of machining to provide the second plate; forming a surface containing the hydrophilic substance on the top surface of a plate having the corresponding size to the underside surface of the second plate by means of surface treatment to provide the first plate; and bonding the underside surface of the third plate to the top surface of the second plate and bonding the underside surface of the second plate to the top surface of the first plate.

The inlet and the outlet of the third plate and the two or more reaction chambers of the second plate are formed by means of a machining method selected from the group consisting of injection molding, hot-embossing, casting, and laser ablation. Moreover, the hydrophilic substance on the surface of the first plate is treated thereto by means of a method selected from the group consisting of oxygen and argon plasma treatment, corona discharge, and surface active agent coating, and the treatment of the hydrophilic substance is conducted in a manner known in the art. Also, the bonding of the underside surface of the third plate to the top surface of the second plate and the bonding of the underside surface of the second plate to the top surface of the first plate are carried out by means of thermal bonding, ultrasonic welding, solvent bonding, hot plate welding, ultraviolet bonding, and press bonding in a manner known in the art. Furthermore, double-sided adhesives, thermoplastic resin or thermosetting resin may be treated to the spaces between the third plate and the second plate and between the second plate and the first plate.

Figure 10:
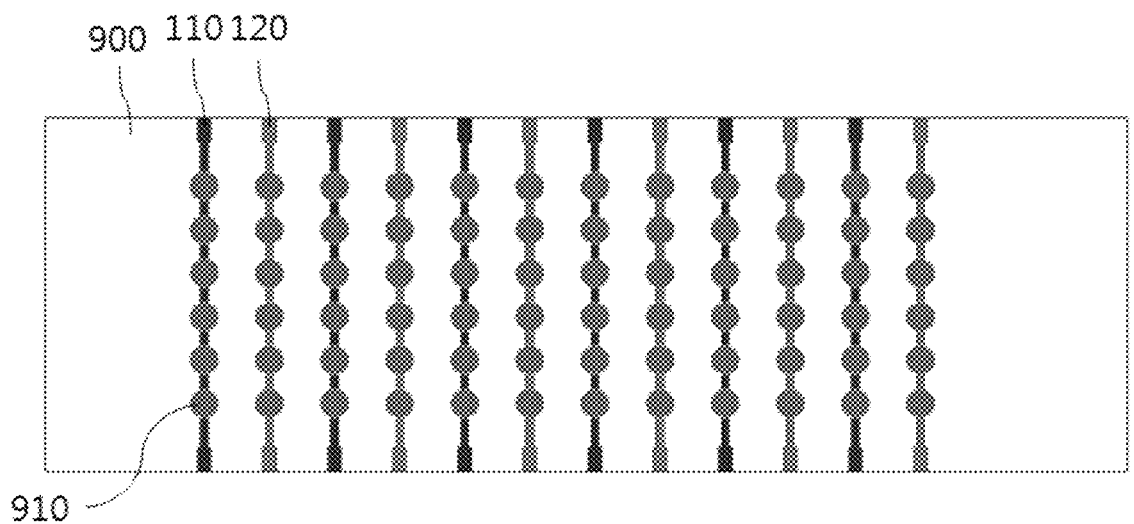
FIGS. 10 to 12 are views showing a state where the PCR chips 900 of various types and the PCR thermal block get in contact with each other.
Figure 11:
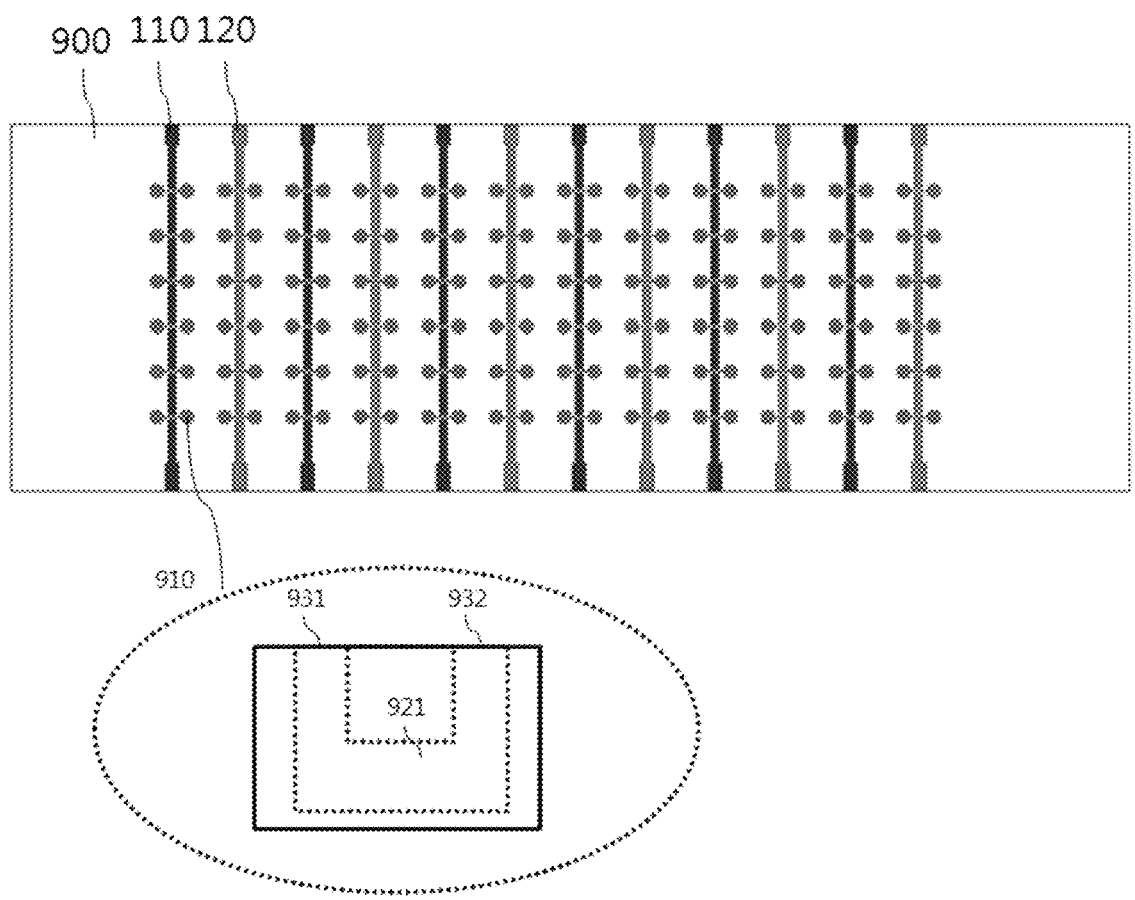
Figure 12:
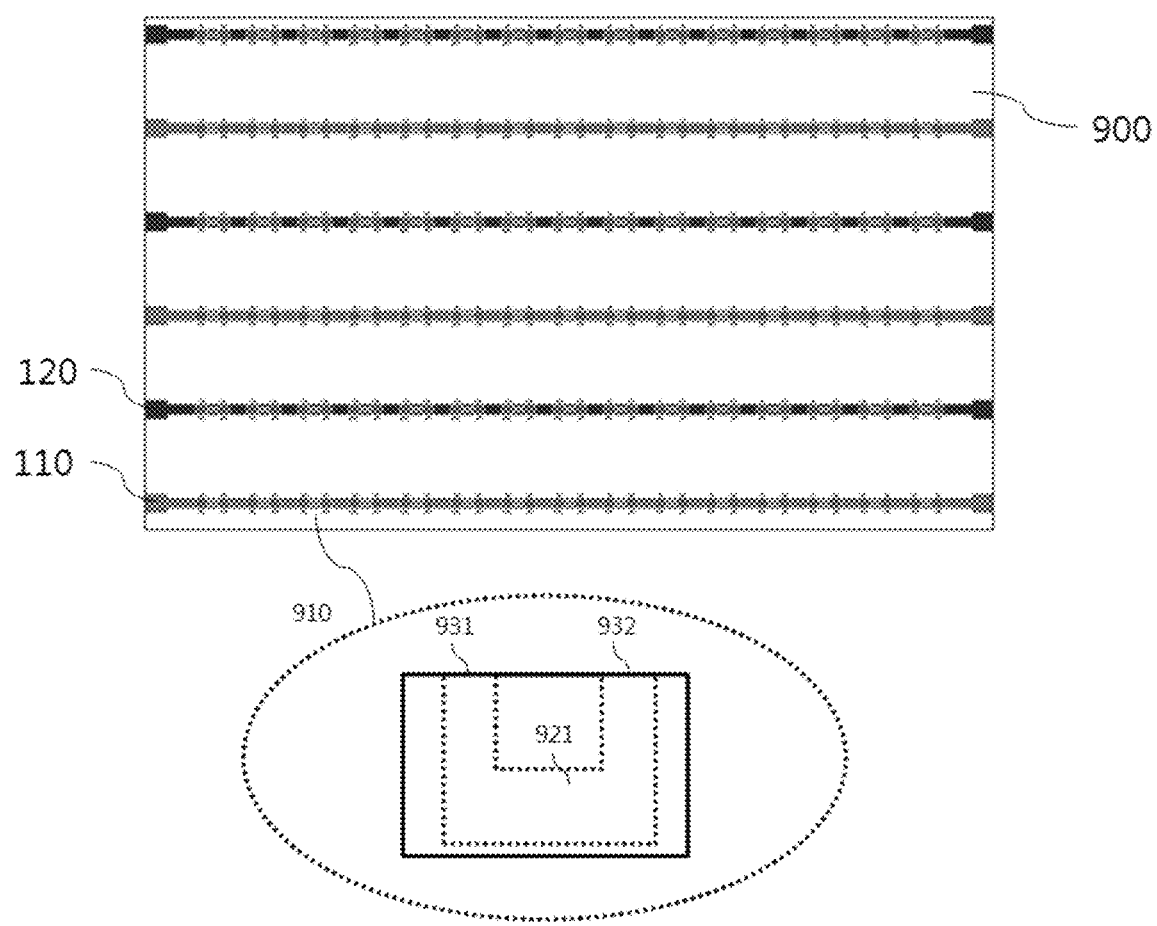

FIGS. 10 to 12 are views showing a state where the PCR chips 900 of various types and the PCR thermal block get in contact with each other.

Referring to FIG. 10, the PCR chip 900 includes the reaction chambers 910 of the integrated inlet and outlet well type, and the reaction chambers 910 are arranged on the heaters 110 and 120 of the PCR thermal block to correspond to each other. Referring to FIG. 11, the PCR chip 900 includes the reaction chambers 910 of the separate inlet and outlet channel type, and the reaction chambers 910 are arranged on the heaters 110 and 120 of the PCR thermal block to vertically correspond to each other. Moreover, referring to FIG. 12, the PCR chip 900 includes the reaction chambers 910 of the separate inlet and outlet channel type, and the reaction chambers 910 are arranged on the heaters 110 and 120 of the PCR thermal block to horizontally correspond to each other.

Figure 13:
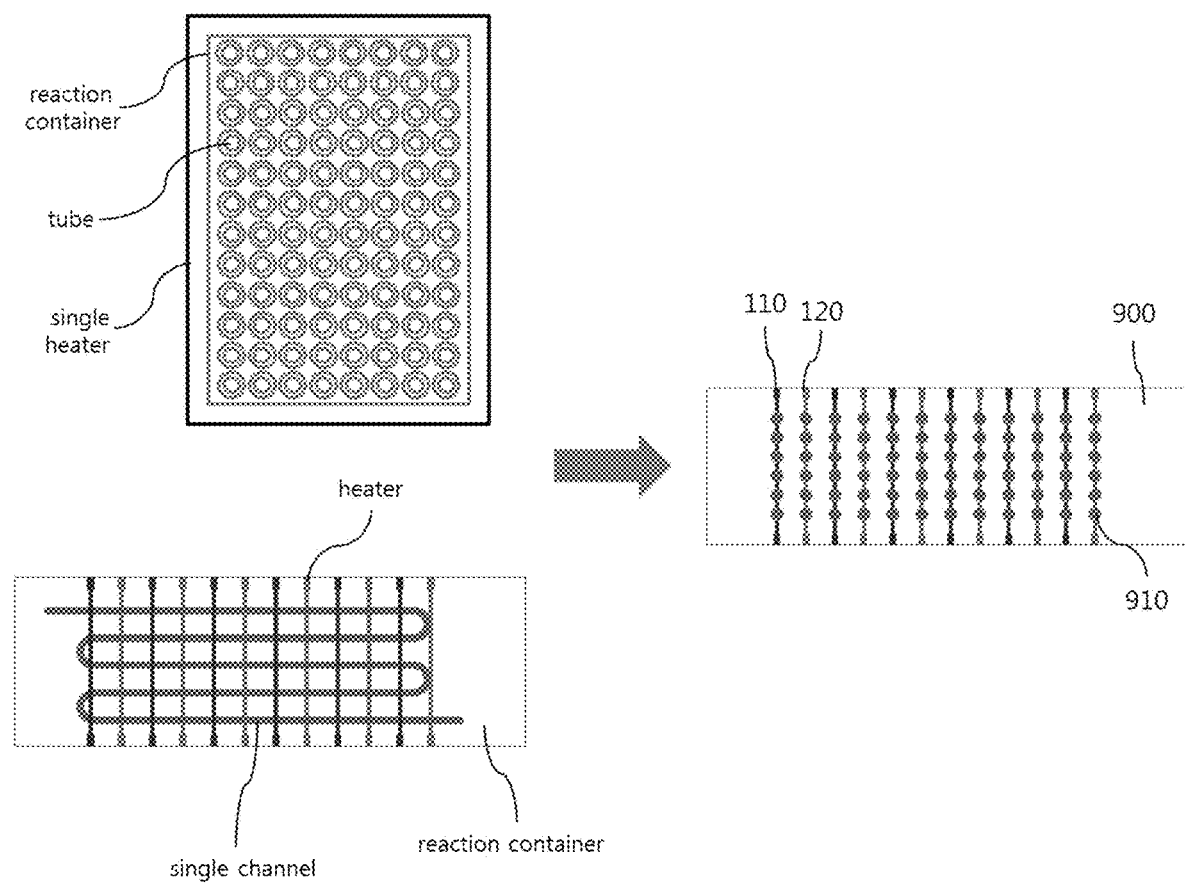
FIGS. 13 and 14 are comparative views showing comparison between the PCR chip according to the preferred embodiment of the present invention and the conventional PCR reaction container of the tube type and the flow channel type.
Figure 14:
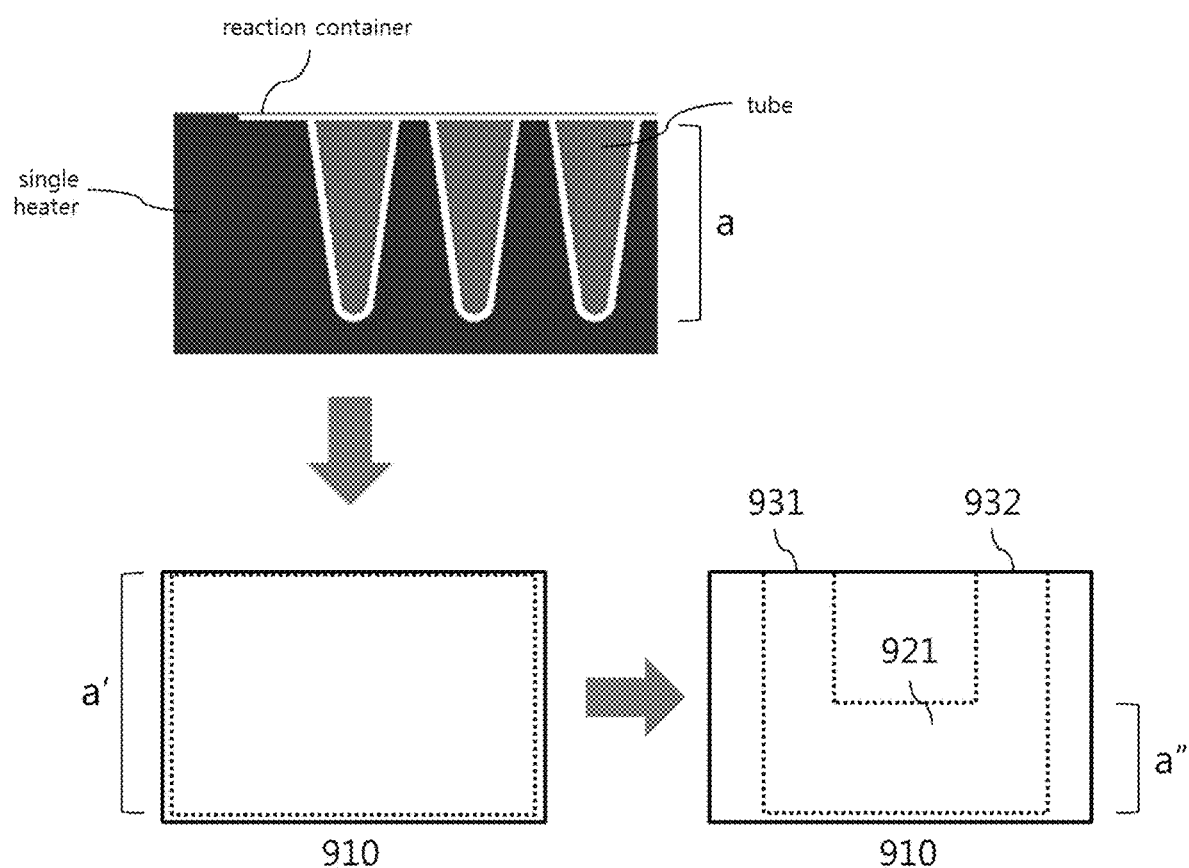

Such a PCR chip according to the embodiment of the present invention increases density of PCR device implementation more than the conventional PCR reaction container and contributes to effective PCR execution. Referring to FIG. 13, the PCR chip according to the present invention can simultaneously execute the PCR on more samples of various kinds than the conventional PCR reaction container of the tube type having the single heater, considerably reduce PCR time, and remarkably reduce the size of the container. Furthermore, the PCR chip according to the present invention can simultaneously execute the PCR on more samples of various kinds than the conventional PCR reaction container of the single channel type having the plural heaters, reduce PCR time for lots of samples, and remarkably increase density of the PCR device because the PCR chip according to the present invention does not need a fluid control module through the channel. In the meantime, referring to FIG. 14, another PCR chip according to an embodiment of the present invention can minimize the volume of samples due to miniaturization of the PCR chip and increase a thermal contact surface between the heater, namely, the thermal block, and the samples so as to increase the surface to volume ratio ($a<a'<a''$). In this instance, out of the PCR chips according to the embodiments of the present invention, the PCR chip shown in FIGS. 11 and 12 is more improved in the surface to volume ratio than the PCR chip shown in FIG. 10.

Figure 15:
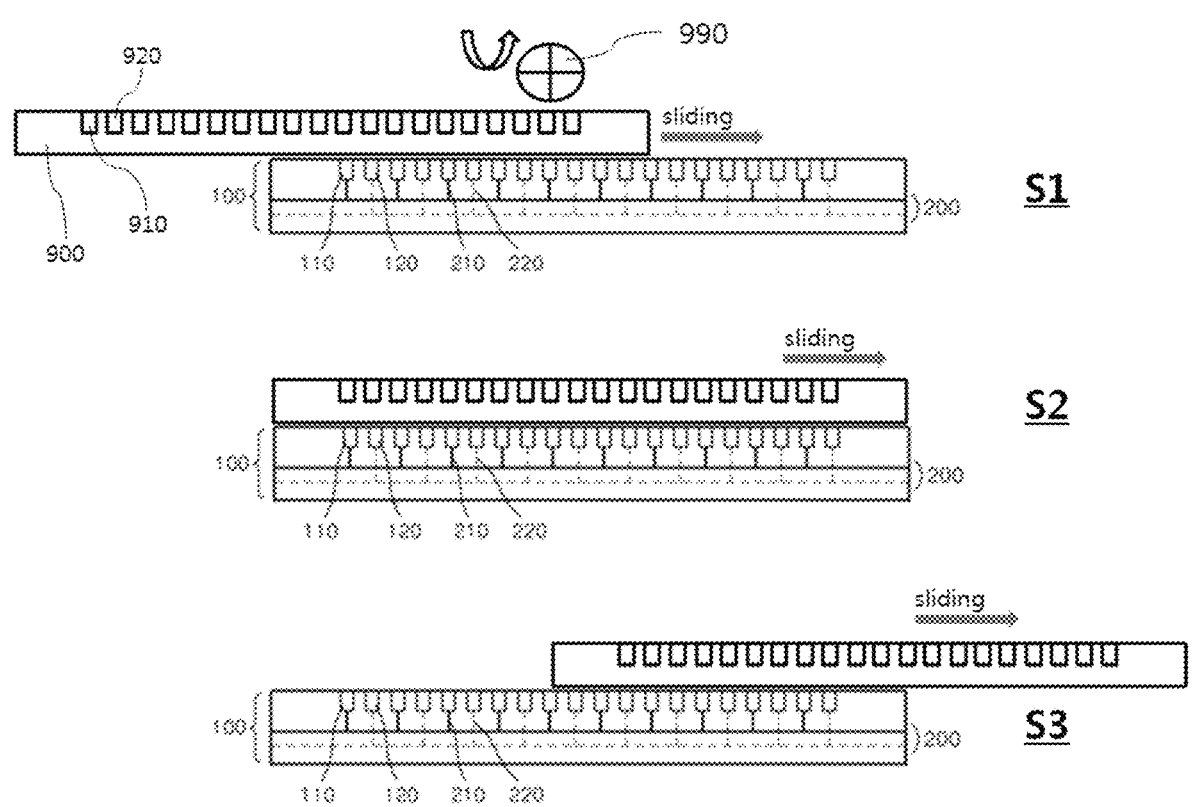
FIG. 15 is a view showing a unidirectional sliding means and a PCR execution principle using the unidirectional sliding means according to a preferred embodiment of the present invention.

FIG. 15 is a view showing a unidirectional sliding means and a PCR execution principle using the unidirectional sliding means according to a preferred embodiment of the present invention.

Referring to FIG. 15, the steps (S1 to S3) of executing the PCR through the PCR device which includes the PCR thermal block 100, the power supply part 200, the PCR chip 900 and the unidirectional sliding means 990 will be described. The unidirectional sliding means 990 slides while maintaining the contact between the PCR chip 900 and the PCR thermal block 100 in the state where the PCR chip 900 is mounted. When the unidirectional sliding means slides, a sequential thermal contact occurs between the two or more reaction chambers 910 which are repeatedly arranged from one end of the PCR chip 900 to the other end the two or more heaters 110 and 120 which are arranged from one end of the PCR thermal block 100 to the other end.

At a first step, prepare the PCR solution having double-stranded target DNA, oligonucleotide primer having the complimentary sequence to specific sequence to be amplified, DNA polymerase, deoxyribonucleotide triphosphates (dNTP), and PCR buffer. After that, introduce the PCR solution into the reaction chambers of the PCR chip 900, and then, seal the reaction chambers. After that, connect the power supply part 200, in detail, the first wire 210 and the second wire 220, are connected with the power supply source. Next, Heat the first heater 110 and the second heater 120 through the first wire 210 and the second wire 220, and maintain temperature for PCR execution, namely, temperature (95° C.) for the PCR denaturing step in case of the first heater 110 and temperature (72° C.) for the PCR annealing/extension step in case of the second heater 120.

In the steps S1 to S3, the two or more reaction chambers 910 of the PCR chip 900 accommodate the same or different PCR samples and reagents, and the heaters 110 and 120 repeatedly arranged on the PCR thermal block 100 are based upon the premise to carry out the two steps for the PCR by power supply of the power supply part 200, that is, to maintain the temperature, 95° C., for the denaturing step by the first heater 110, to maintain the temperature, 72° C., for the annealing/extension step by the second heater 120, and to repeatedly maintain the temperatures, 95° C. and 72° C., by 20 heaters.

Referring to the S1 step, the PCR chip 900 by the unidirectional sliding means 990 starts contact with one end of the PCR thermal block 100 and starts to slide. In other words, the first reaction chamber 910 of the right side end of the PCR chip 900 comes into thermal contact with the first heater 110 of the left side end of the PCR thermal block 100 and carries out the denaturing step so as to start the PCR.

Referring to the S2 step, the PCR chip 900 by the unidirectional sliding means 990 continuously slides while keeping the contact with the upper surface of the thermal block 100 to execute the PCR sequentially. For instance, by the sliding of the PCR chip 900, the first reaction chamber 910 of the right side end of the PCR chip 900 gets in thermal contact with the second heater 120 of the left side end of the thermal block 100 to carry out the annealing/extension step and the second reaction chamber 920 of the right side end of the PCR chip 900 gets in thermal contact with the first heater 110 of the left side end of the PCR thermal block 100 to carry out the denaturing step, so that the PCR chip 900 sequentially execute the PCR by repeating the thermal contact between the reaction chambers repeatedly arranged at the right side end of the PCR chip 900 and the heaters repeatedly arranged at the left side end of the PCR thermal block 100.

Referring to the S3 step, the PCR chip 900 by the unidirectional sliding means 990 slides while getting in contact with the upper surface of the thermal block 100, and then, finishes the PCR. For instance, the reaction chamber of the left side end of the PCR chip 900 gets in thermal contact with the heater of the right side end of the thermal block 100 to carry out the annealing/extension step, thus finishing the PCR executed sequentially.

In the meantime, after the steps of S1 and S2, of course, the unidirectional sliding means 990 can repeat the steps of S1 to S3 through reverse sliding after executing the PCR through the forward sliding. Therefore, the PCR device according to the embodiment of the present invention can rapidly execute the PCR while maintaining the thermal contact between the PCR thermal block and the PCR chip having the PCR chamber without using various complicated control modules, thereby achieving miniaturization and integration of the device.

Figure 16A:
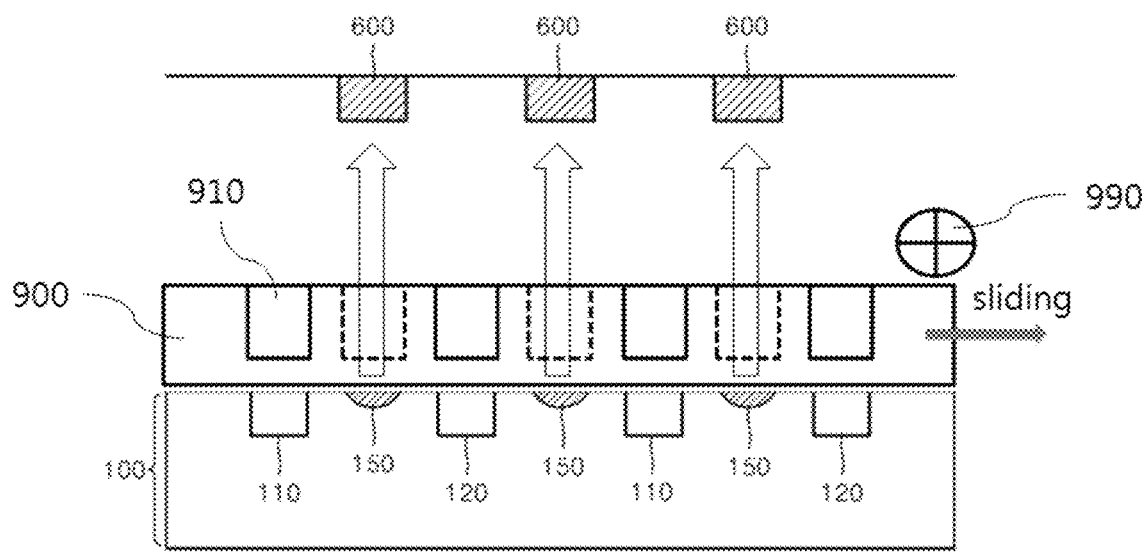
FIGS. 16A to 18 are views showing real-time PCR realized through various PCR devices according to preferred embodiments of the present invention.
Figure 16B:
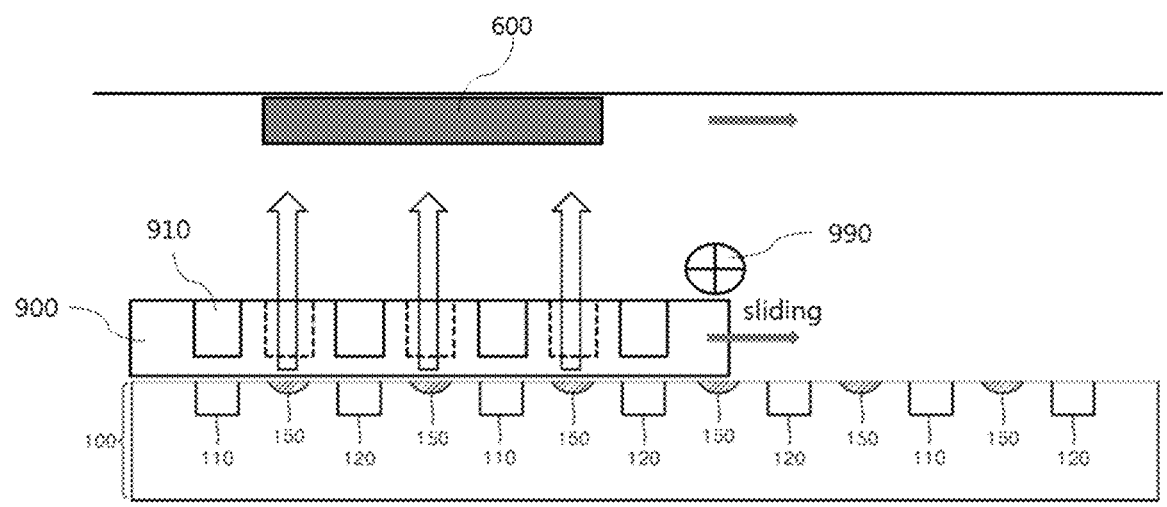
Figure 16C:
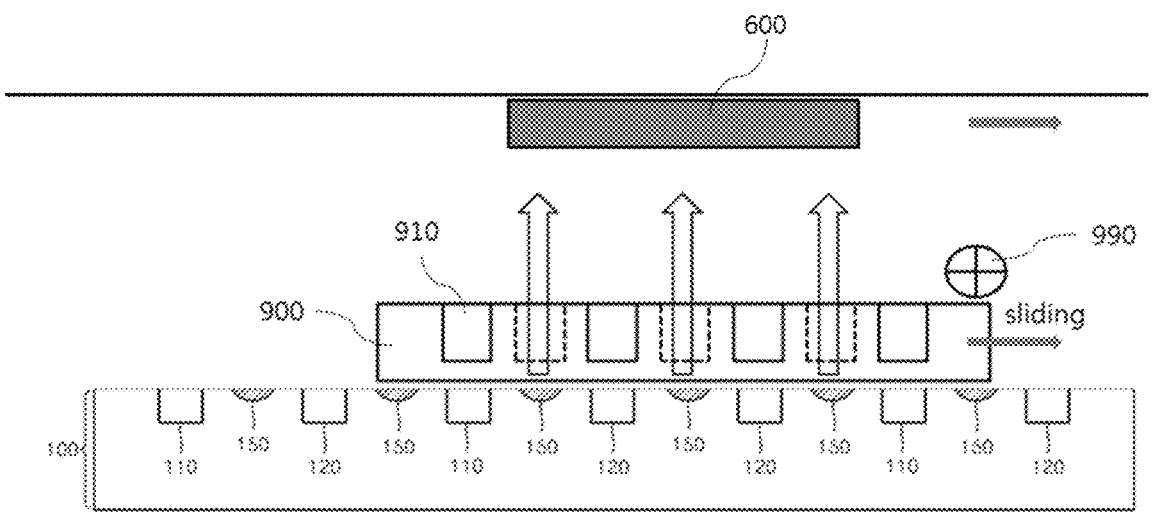
Figure 16D:
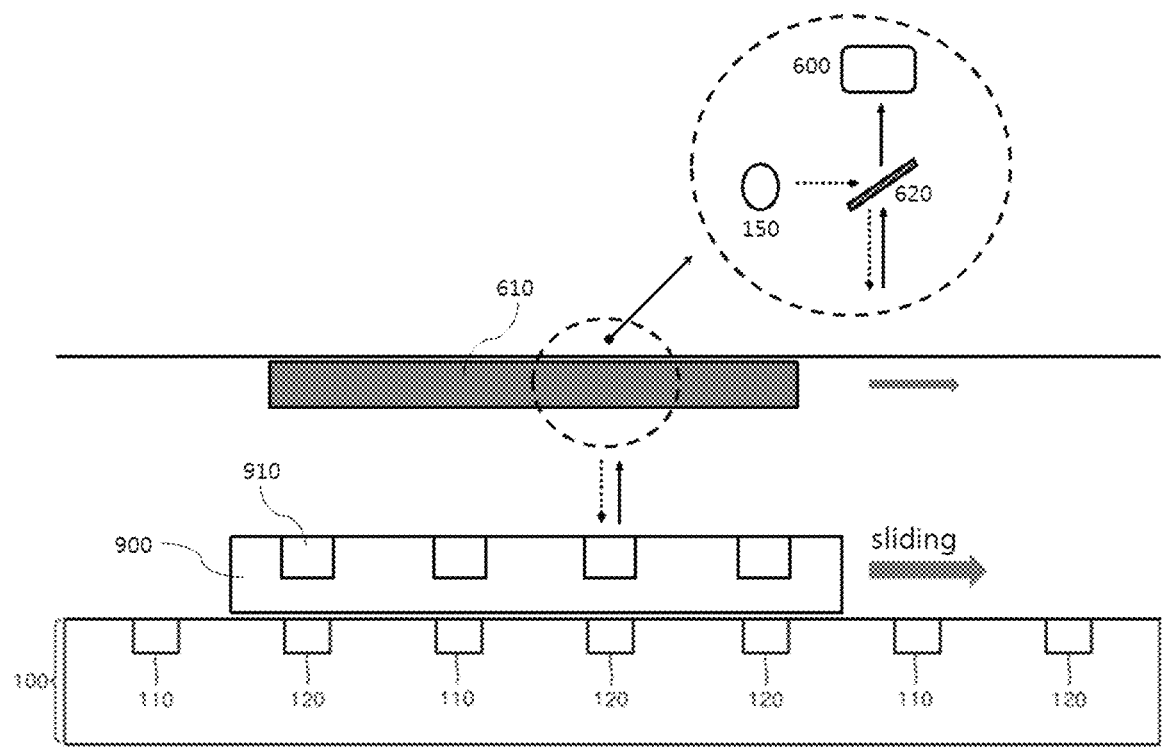
Figure 17:
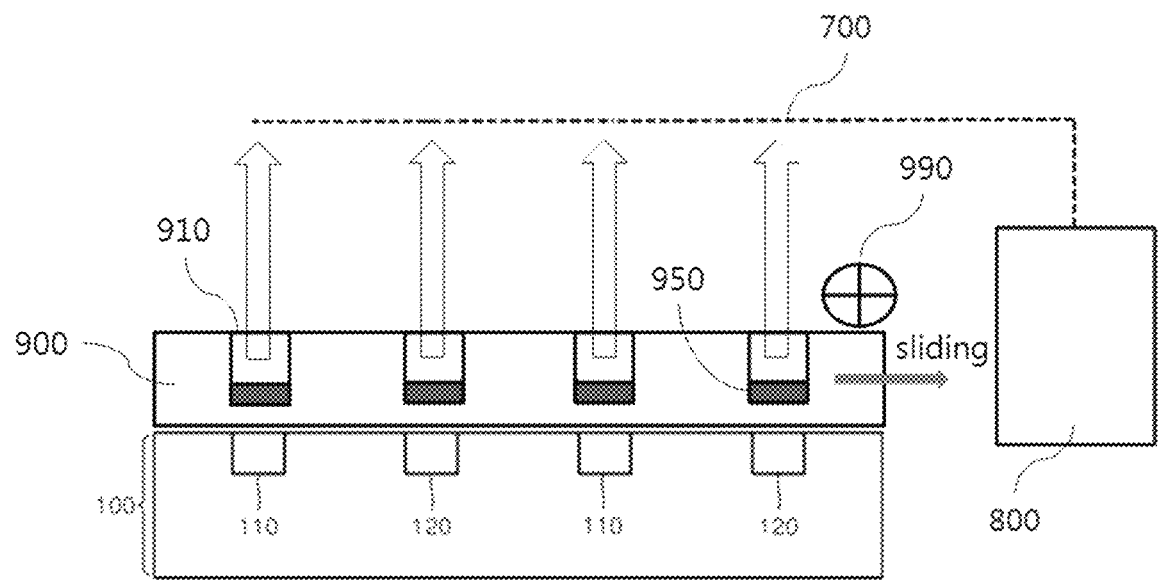
Figure 18:
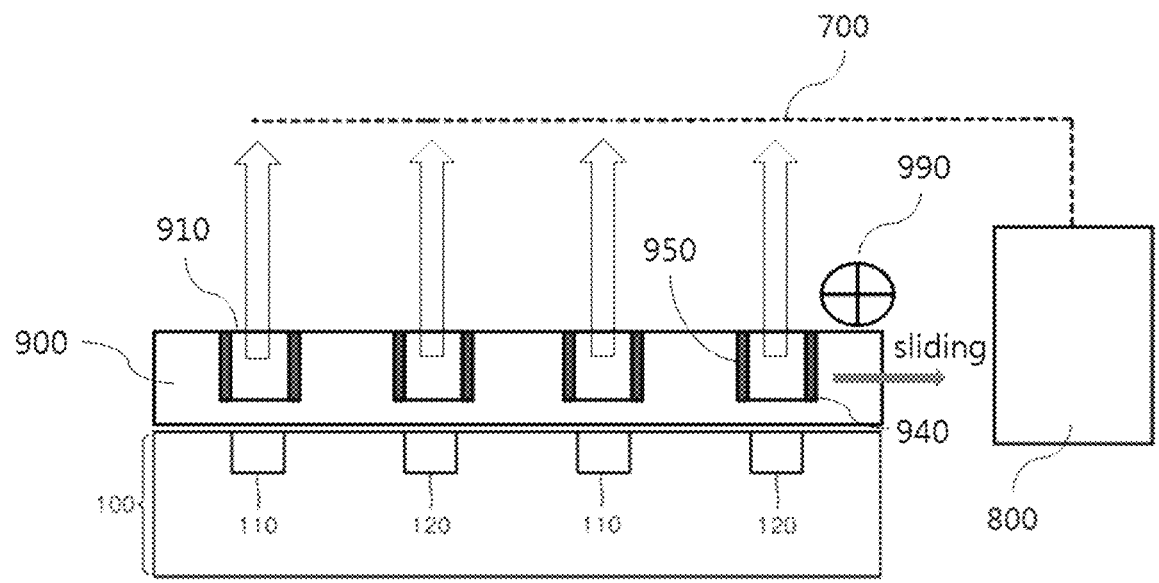

FIGS. 16 to 18 are views showing real-time PCR realized through various PCR devices according to an embodiment of the present invention.

FIGS. 16A to 16D illustrate real-time PCR realized through the PCR device according to an embodiment of the present invention. The PCR device includes an optical module for measuring the nucleic acids amplification occurring inside the reaction chamber 910 of the PCR chip 900 in real time. The optical module includes: a light source 150 for supplying light to the reaction chamber 910 of the PCR chip 900; and a light detector 600 arranged to accommodate the light emitted from the PCR chip 900. In order to measure the nucleic acids amplification in real time using the optical module, a fluorescent material is added to the target sample solution and emits light by light having a specific wavelength according to the production of PCR products, thus generating optical signals to be measurable and analyzable. The light source 150 is selected from the group consisting of mercury arc lamp, xenon arc lamp, tungsten arc lamp, metal halide arc lamp, metal halide fiber, and light-emitting diodes. Furthermore, the light source 150 has a wavelength in the range of about 200 to 1300 nm, and otherwise, may have a multi-wavelength through multiple light sources or filters. Additionally, the light detector 600 is selected from the group consisting of charge-coupled device (CCD), charge-injection device (CID), complementary-metal-oxide-semiconductor detector (CMOS), and photo multiplier tube (PMT). In the meantime, in one embodiment of the present invention, the light source 150 and the light detector 600 may be drivably connected with various modules in order to improve detection efficiency. For instance, the light source 150 may further include or may be drivably connected with one or more optical band pass filters which can pass only light of the wavelength band capable of exciting the fluorescent material, and the light detector 600 may further include or may be drivably connected with one or more optical band pass filter which can pass only light of the emitted wavelength band of the fluorescent material. In this instance, the light source 150 or the light detector 600 may further include or may be drivably connected with a substituent part capable of coinciding the excited wavelength and the light-emitted wavelength of the fluorescent material with each other in the one or more optical band pass filter. Additionally, the light source 150 may further include or may be drivably connected with a light emitting diode (LED) using one or more wavelengths to excite one or more fluorescent materials. In this instance, the light source 150 may further include or may be drivably connected with a substituent part capable of coinciding the excited wavelength and the light-emitted wavelength of the one or more fluorescent materials with each other in the LED light source.

Referring to FIG. 16A, the PCR device includes: the PCR chip 900 made of a light transmissive material, the light source 150 arranged between the first heater 110 and the second heater 120 of the PCR thermal block 100; and a light detector 600 for detecting an optical signal emitted from the light source 150. In detail, the PCR solution having the target sample solution slides portions corresponding to the upper portion of the first heater 110 and portion corresponding to the upper portion of the second heater 120 in each reaction chamber 910, thus carrying out the PCR denaturing step and the PCR annealing/extension step. In this case, the target sample solution passes through portion corresponding to the upper portion of the light source 150 between the first heater 110 and the second heater 120 and between heater units each having the first heater 110 and the second heater 120. When the reaction chamber 910 containing the target sample solution passes through the portion corresponding to the upper portion of the light source 150, the PCR chip 900 moves slowly or momentarily stops through control of the unidirectional sliding means 990. After that, light is emitted from the light source 150, the emitted light passes the PCR chip 900, in detail, the reaction chamber 910, and then, the light detector 600 measures and analyzes the optical signal generated by the nucleic acids amplification in the reaction chamber 910. During the PCR cycles, accordingly, the reaction results of the nucleic acids (coupled to the fluorescent material) amplification in the reaction channels 303 are monitored in real time, thus allowing the quantity of target DNA to be measured and analyzed in real time.

Differently from the PCR device shown in FIG. 16A, the PCR device shown in FIGS. 16B to 16C includes: the PCR chip 900 made of a transflective material in such a way that an upper layer is made of a transmissive material but a lower layer is made of a non-transmissive material; the light source 150 arranged between the first heater 110 and the second heater 120 of the PCR thermal block 100; and the light detector 600 which moves corresponding to a movement route of the PCR chip 900 in order to detect the optical signal emitted from the light source 150. In this instance, of course, the light detector 600 is fixed but the light source 150 is capable of moving corresponding to the movement route of the PCR chip 900. In the meantime, the PCR device according to FIG. 16D includes: the PCR chip 900 made of a transflective material in such a way that an upper layer is made of a transmissive material but a lower layer is made of a non-transmissive material; and an optical module 610 which moves corresponding to the movement route of the PCR chip 900 and in which the light source 150, the light detector 600 for detecting the optical signal emitted from the light source 150 and a dichroic mirror 620 transferring the light emitted from the light source 150 to the reaction chamber 600 of the PCR chip 900 and transferring the light emitted from the reaction chamber 910 to the light detector 600 are accommodated.

FIG. 17 illustrates the real-time PCR executed through a PCR device according to another embodiment of the present invention. The PCR device includes a PCR thermal block 100, a PCR chip 900, unidirectional sliding means 990 and an electrochemical module for real-time measurement. In detail, the PCR chip 900 includes a detection electrode 950 for detecting an electrochemical signal generated by combination of amplified nucleic acids and redox indicators inside the reaction chamber 910.

The electrochemical module includes a module to electrochemically measure nucleic acids amplification occurring inside the reaction chamber 910 of the PCR chip 900 in real time. The electrochemical module may be implemented in various ways to achieve the purpose, but preferably, as shown in FIG. 17, includes: a detection electrode 950 for detecting an electrochemical signal generated by combination of the amplified nucleic acids and the redox indicators inside the reaction chamber 910 of the PCR chip 900; electrically connecting means 700 linked with the detection electrode 950; and an electrochemical signal measuring module 800 for measuring the detected signal through the electrically connecting means 700.

The redox indicator is chemically reacted (bonded) to the amplified nucleic acids and thus generates electrochemical signals, and the electrochemical signals are successively detected and measured according to the continuous amplification of the nucleic acids. For example, the double-stranded DNA generally has negative charge, and if the redox indicator has positive charge, the amplified nucleic acids are reacted to the redox indicator according to the continuous amplification of the nucleic acids to produce the detectable signals through the variations of total quantity of charge. Accordingly, the electrochemical signals are generated by the variations of total current values caused by the bonding of the negative charge of the amplified nucleic acids and the positive charge of the redox indicator, and the redox indicator may be a cationoid among the ionized products of an ionic bonding substance. In more detail, the ionic bonding substance is methylene blue, and the redox indicator is a cationoid among the ionized products of the methylene blue. If the methylene blue $C16H18N3SCl \cdot 3H2O$ is melted in a solvent, it becomes ionized to $C16H18N3S\text{<+>}$ and $Cl\text{<-->}$ and has positive charge by sulfur S. The double-stranded DNA consists of sugar, base, and phosphate, and the phosphate generally has negative charge. Accordingly, the double-stranded DNA has negative charge. The positive ion of methylene blue is bonded to phosphate of DNA, so that the apparent diffusion rate of methylene blue bonded to the double-stranded DNA becomes more decreased than that of methylene blue, and accordingly, the peak value of the current is reduced. During the PCR cycles, accordingly, the double-stranded DNA is amplified and the quantity of methylene blue bonded to the double-stranded DNA is increased, thus reducing the peak value of current, so that the quantity of the amplified nucleic acids can be in real time measured through the electrical signals generated by the chemical bonding of the real time amplified PCR products and the methylene blue.

The detection electrode 950 may be made of various materials capable of detecting the electrochemical signal generated by means of the bonding of the amplified nucleic acids with the redox indicator from the interior of the reaction chamber 910. For example, the detection electrode 950 is made of one or more materials selected from the group consisting of Au, Co, Pt, Ag, carbon nanotube, graphene, and carbon. In the meantime, the detection electrode 950 may be formed in various shapes and standards in order to maximize efficiency. For instance, the detection electrode is formed of a two-electrode module including a working electrode on which the amplified nucleic acids and the redox indicator are bonded to each other and a reference electrode on which bonding between the amplified nucleic acids and the redox indicator does not occur so that it is functioned as a measuring reference of electrode potential. For instance, the detection electrode is formed of a three-electrode module including the working electrode, the reference electrode, and the counter electrode along which the current generated from the working electrode flows. If the detection electrode 950 is configured as a multiple electrode module, like this, the sensitivity of the electrochemical signals generated in the reaction chamber can be enhanced, and further, the detection and measurement of the generated signals can be easily conducted.

The electrochemical signal measuring module 800 is electrically connected to a connection port of a holder (not shown) of the PCR chip 900 by electrically connecting means 700 like a lead wire. Accordingly, the electrochemical signals repeatedly generated through the successive nucleic acids amplification from the interior of the reaction chamber 910 of the PCR chip 900 are sequentially detected through the detection electrode 950 of the PCR chip 900, and the detected signals are measured and further processed or analyzed in the electrochemical signal measuring module 800 through the electrically connecting means 700. The electrochemical signal measuring module 800 is provided in various manners, and preferably, it is selected from the group consisting of anodic stripping voltammetry (ASV), chronoamperometry (CA), cyclic voltammetry, square wave voltammetry (SWV), differential pulse voltammetry (DPV), and impedance.

Referring to FIG. 17, the real time PCR device can measure and analyze the nucleic acids amplification in real time during the PCR. In this instance, unlike the first PCR device according to the embodiment of the present invention, there is no need to add a fluorescent material to the PCR solution. For instance, by the sliding of the PCR chip 900, the PCR sample and reagent solution are successively passed through the portion corresponding to the upper portion of the first heater 110 and the portion corresponding to the upper portion of the second heater 120 in the reaction chamber 910, thus carrying out the PCR denaturing step and the PCR annealing/extension step. In this case, the amplified nucleic acids flows slowly or momentarily stops at any position between the first heater 110 and the second heater 120 through control of the unidirectional sliding means 990. After that, the electrochemical signals generated by the bonding of the amplified nucleic acids to the redox indicator are successively detected in real time and measured through the detection electrode 950. During the PCR cycles, accordingly, the reaction results of the nucleic acids amplification in the reaction chamber 910 (having no fluorescent material and light detection system) are monitored in real time, thus allowing the quantity of target DNA to be measured and analyzed in real time.

FIG. 18 illustrates real-time PCR executed through another type of the PCR device according to an embodiment of the present invention. The PCR device includes the PCR thermal block 100, the PCR chip 900, the unidirectional sliding means 990, and the electrochemical module for measuring in real time. In detail, the PCR chip 900 includes: an immobilization layer 940 formed on one region of the interior of the reaction chamber 910 and subjected to surface treatment with a capture probe capable of being complementarily bonded to one region of the amplified target nucleic acids; and a detection electrode 950 formed on the other region of the reaction chamber 910 so as to detect electrochemical signals. The reaction chamber may include composites having metal nanoparticles and signaling probes connected to the metal nanoparticles in such a manner as to be complementarily bonded to the other region of the amplified target nucleic acids.

The electrochemical module may include a module for electrochemically measuring nucleic acids amplification occurring inside the reaction chamber 910 of the PCR chip 900 in real time. The electrochemical module may be implemented in various ways to achieve the purpose, but preferably, includes: an immobilization layer 940 formed on one region of the interior of the reaction chamber 910 and subjected to surface treatment with a capture probe capable of being complementarily bonded to one region of the amplified target nucleic acids; a detection electrode 950 formed at the other area of the interior of the reaction chamber 910 to detect electrochemical signals; electrically connecting means 700 linked with the detection electrode 950; and an electrochemical signal measuring module 800 for measuring the detected signal by means of the electrically connecting means 700. In this instance, the reaction chamber 910 may include composites having metal nanoparticles and signaling probes connected to the metal nanoparticles in such a manner as to be complementarily bonded to the other region of the amplified target nucleic acids.

The immobilization layers 940 and the detection electrode 950 are located at various positions of the reaction chamber 910, and, preferably, they face each other in up and down directions or in left and right directions. Further, the reaction chamber 910 contains the composites accommodated thereinto, and the composites include the metal nanoparticles and the signaling probes connected to the metal nanoparticles and complementarily bonded to the other region of the amplified target nucleic acids. In this case, the composites are previously contained in the reaction chamber 910 before the PCR sample containing the template nucleic acids are introduced, and otherwise, they are introduced into the reaction chamber 910 in the state of being contained in the PCR reagents like primer and polymerase. The immobilization layer 940 is made of various materials like silicone, plastic, glass and metal materials so that the capture probe is deposited and exposed on one surface thereof. Before the deposition of the capture probe, the surface of the immobilization layer 940 is first subjected to surface treatment with a material like amine group ($NH_3^+$), aldehyde group (—COH), and carboxyl group (—COOH). The capture probe is complementarily bonded to one portion (region) of the amplified target nucleic acids and forms the composites through the bonding to the metal nanoparticles. The metal nanoparticles are made of various metals, and preferably, they are made of one or more materials selected from the group consisting of Zn, Cd, Pb, Cu, Ga, In, Au, Cr, Mn, Fe, Co, Ni, Cs, Ba, Cd, Hg, As, Se, Sn, Sb, Bi and Ag. The signaling probe is complementarily bonded to one region of the amplified target nucleic acids, and in this case, the complementarily bonded region of the amplified target nucleic acids to the signaling probe is different from that to the capture probe. Accordingly, the capture probe and the signaling probe can be complementarily bonded to the amplified target nucleic acids. If the target nucleic acids are amplified in the reaction chamber 910 during the PCR, that is, the amplified target nucleic acids are complementarily bonded to the capture probe treated on the surface of the immobilization layer 940 and further complementarily bonded to the signaling probe connected to the metal nanoparticles, thus allowing the metal nanoparticles to be collected to the region adjacent to the immobilization layer 940. As a result, the metal nanoparticles do not reach the detection electrode 950, thus causing the current variations (reduction) between the metal nanoparticles and the detection electrode 950 and generating detectable electrochemical signals according to the amplification of the target DNA. On the other hand, the amplified target nucleic acids, the capture probe and the signaling probe are formed of single-stranded DNA.

The detection electrode 950 is disposed on at least one region of the reaction chamber 910 to detect the electrochemical signals generated in the interior of the reaction chamber 910. So as to conduct the detection, the detection electrode 950 is made of various materials, and for example, is made of one or more materials selected from the group consisting of Au, Co, Pt, Ag, carbon nanotube, graphene, and carbon. Further, the detection electrode 950 has various shapes and structures capable of effectively detecting the electrochemical signals generated in the interior of the reaction chamber 910, and for example, has a shape of a plate made of a metal material disposed along the inner surfaces of the reaction chamber 910. On the other hand, the electrochemical signals are measured by an electrochemical signal measuring module, and the electrochemical signal measuring module is provided in various manners. Preferably, the electrochemical signal measuring module is selected from the group consisting of anodic stripping voltammetry (ASV), chronoamperometry (CA), cyclic voltammetry, square wave voltammetry (SWV), differential pulse voltammetry (DPV), and impedance. The electrochemical signals are generated from the current variations caused by the complementary bonding of the amplified target nucleic acids to the capture probe and the signaling probe. The process in which the electrochemical signals are generated in the PCR device according to the present invention is as follows. At a first step, before the PCR starts, the capture probe treated on the surface of the immobilization layer and the composites (signaling probe-metal nanoparticles) including the signaling probe and the metal nanoparticles is in its original state, at a second step, current variations (signals) are generated from the reduction or oxidation between the working electrode and the metal nanoparticles, and at a third step, after the PCR has started, the amplified target nucleic acids are bonded to the capture probe and the signaling probe of the composites to cause the reduction of the current variations (signals). In more detail, if the reduction voltage is applied to the metal nanoparticles of the composites, the metal nanoparticles are collected to the surface adjacent to the working electrode and thus form an accumulation layer while being reduced. Then, if a voltage is applied to the working electrode, the reduced metal nanoparticles are oxidized (stripped) to generate the current variations (signals), and the current variations are easily measured through the voltage values indicated by the oxidation current peaks. In this case, the current variation values, that is, the electrochemical signals generated in the interior of the reaction chamber 910 indicate the quantity of variations of the target nucleic acids (target DNA). Also, the voltage values at which the metal nanoparticles are oxidized are different in accordance with the kinds of the metal nanoparticles, and in case of two kinds of metal nanoparticles, accordingly, the signals for two or more samples can be detected at the same time. After that, if the PCR is conducted, the target DNA is amplified from the template DNA, and the amplified target nucleic acids are complementarily bonded (hybridized target DNA) to the capture probe and the signal probe of the composites (signaling probe-metal nanoparticles), thus inhibiting the accumulation of the metal nanoparticles of the composites and decreasing the current values. As the PCR cycles are increased, further, the quantity of the amplified target nucleic acids are increased to allow the complementarily bonding (hybridized target DNA) to the capture probe and the signal probe of the composites to be raised, thus more decreasing the current values. Accordingly, the reduction of the current variations, that is, the electrochemical signals are detected and measured, thus conducting the PCR in real time.

In the meantime, the detection electrode 950 may be formed in various ways. For instance, the detection electrode 950 is formed of a two-electrode module including a working electrode 950*a* on which oxidation or reduction reaction occurs and a reference electrode 950*b* on which oxidation or reduction reaction does not occur. Referring to FIG. 16, the detection electrode 950 is formed of a three-electrode module including the working electrode 950*a*, the reference electrode 950*b*, and a counter electrode 950*c* for adjusting the balance of electrodes generated from the working electrode 950*a*. If the detection electrode 950 is configured as a multiple electrode module, like this, the sensitivity of the electrochemical signals generated in the reaction chamber can be enhanced, and further, the detection and measurement of the generated signals can be easily conducted.

Referring to FIG. 18, the electrochemical signal measuring module 800 is electrically connected to a connection port of a chip holder of the PCR chip 900 by electrical connection means 700 like lead wire. Accordingly, the electrochemical signals repeatedly generated through the successive nucleic acid amplification from the interior of the reaction chamber 910 of the PCR chip 900 are sequentially detected through the detection electrode 950 of the PCR reaction chip 900, and the detected signals are measured and further processed or analyzed in the electrochemical signal measuring module 800 through the connection port of the chip holder and the electrical connection means 700. The electrochemical signal measuring module 800 is provided in various manners, and preferably, it is selected from the group consisting of anodic stripping voltammetry (ASV), chronoamperometry (CA), cyclic voltammetry, square wave voltammetry (SWV), differential pulse voltammetry (DPV), and impedance.

Referring to FIG. 18, when the PCR is executed by the PCR device according to the embodiment of the present invention, the nucleic acid amplification process can be measured and analyzed in real time. In this instance, unlike the first PCR device according to the embodiment of the present invention, there is no need to add a fluorescent material to the PCR solution. For instance, by the sliding of the PCR chip 900, the PCR sample and reagent solution are successively passed through the portion corresponding to the upper portion of the first heater 110 and the portion corresponding to the upper portion of the second heater 120 in the reaction chamber 910, thus carrying out the PCR denaturing step and the PCR annealing/extension step. In this case, the amplified nucleic acids flow slowly or momentarily stops at any position between the first heater 110 and the second heater 120 through control of the unidirectional sliding means 990. After that, the electrochemical signals (current change) generated by the complementary bonding of the amplified nucleic acids, the capture probe and the signaling probe of the composites are successively detected and measured in real time through the detection electrode 950. During the PCR cycles, accordingly, the reaction results of the nucleic acid amplification in the reaction chamber 910 (having no fluorescent material and light detection system) are monitored in real time, thus allowing the quantity of target DNA to be measured and analyzed in real time.

Figure 19:
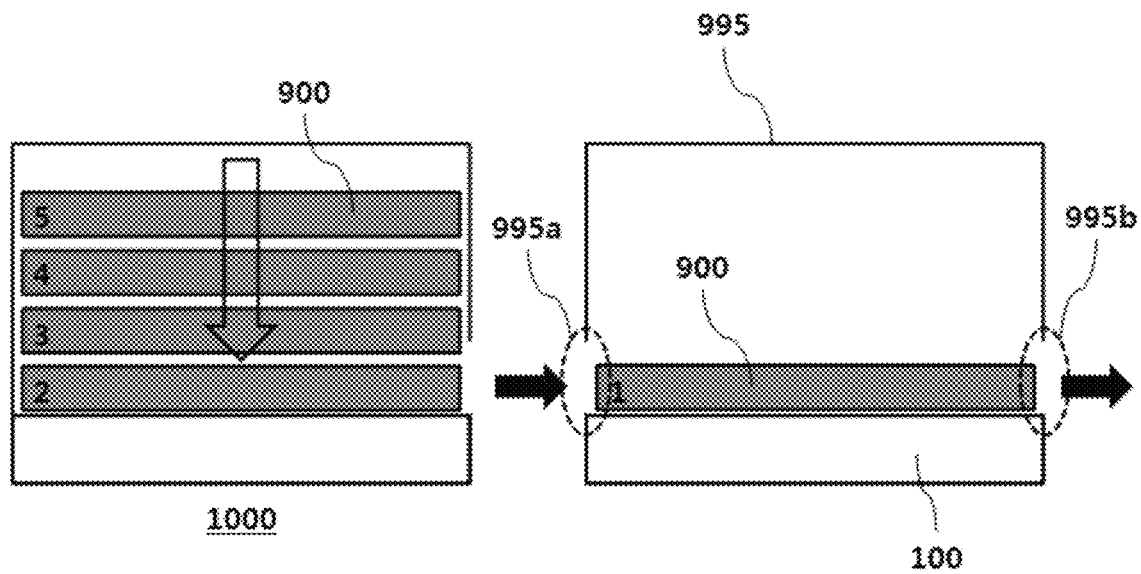
FIG. 19 is a view showing a chip standby part linked with the PCR device.

FIG. 19 is a view showing a chip standby part 1000 linked with the PCR device.

Referring to FIG. 19, the PCR device may further include a chip standby part 1000 for accommodating a plurality of PCR chips 900 having chip numbers 1, 2, 3, 4 and 5, which are drivably connected to each other in such a way that the first PCR chip 900 with the chip number 1 sequentially conducts thermal contact with the PCR thermal blocks 100, and then, the second PCR chip 900 with the chip number 2 starts to conduct thermal contact with the PCR thermal blocks 100. The chip standby part 1000 has a plurality of PCR chips 900 with the chip numbers 1, 2, 3, 4 and 5. The PCR chips accommodated in the chip standby part 1000 may contain various samples, and according to the size of the space, may contain more samples than the five samples contained in the PCR chip illustrated in FIG. 19. For instance, after the PCR thermal blocks 100 and the first PCR chip 900 with the chip number 1 sequentially come into thermal contact with each other, when the first PCR starts, the first PCR chip 900 moves out through a chip outlet 995*b* of a package 995, and then, a chip inlet 995*a* of the package 995 is opened. The second PCR chip 900 with the chip number 2 which is accommodated in the chip standby part 1000 by driving means (not shown) moves above the PCR thermal block 100 to sequentially come into thermal contact with the PCR thermal blocks 100, so that the second PCR starts. In this instance, before the second PCR chip 900 passes through the chip inlet 995*a*, a sensor mounted on the package 995 senses the second PCR chip 900, so that interior conditions of the package 995, for instance, a temperature condition of the PCR thermal blocks 100 and a reaction condition of a PCR measuring device, can be reset. Such a series of processes are repeated until the PCR reaction of the plural PCR chips accommodated in the chip standby part 1000 is finished. The PCR device having such a chip standby part 1000 can execute the PCR on plural samples and reagents rapidly and simultaneously in sequence.

Figure 20:
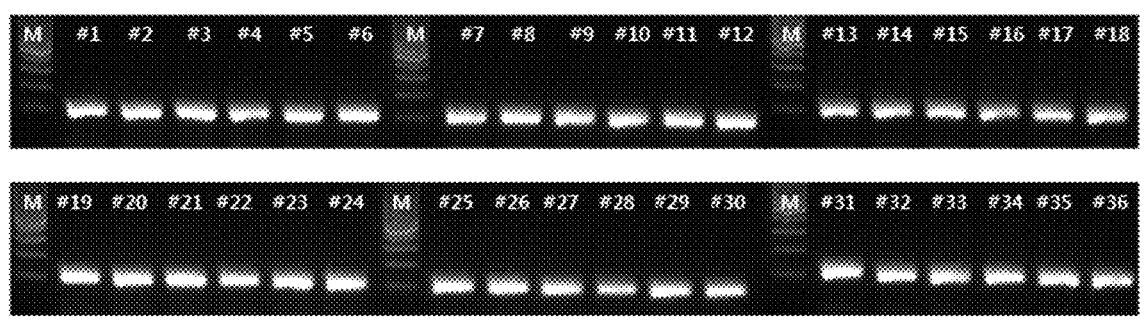
FIG. 20 is an electrophoresis photograph showing a PCR test result of the PCR device.

FIG. 20 is an electrophoresis photograph showing a PCR test result of the PCR device.

Referring to FIG. 20, the results of the PCR using the PCR device according to the embodiment of the present invention can be confirmed. "M" indicated in the electrophoresis photograph means a size marker, and numbers mean sample numbers for the PCR. Through this test, it was confirmed that the PCR could be applied to lots of samples within a short period of time, namely, for about 15 minutes, at the same time. Therefore, the PCR device according to the embodiment of the present invention can remarkably reduce the size of PCR chips, reduce the volume of used samples, considerably reduce the PCR time and execute the PCR to lots of samples, compared with the conventional multi-well type PCR reaction container having the single heater or the conventional single channel type PCR reaction container having multiple heaters. Therefore, the PCR device according to the embodiment of the present invention can effectively solve the problems of the conventional PCR devices.

The invention claimed is:

1. A polymerase chain reaction (PCR) device comprising:
    a PCR thermal block including:
        a first substrate having a flat-plate shape, and
        a plurality of heating units, each of the plurality of heating units having a first heater and a second heater, each of the plurality of heating units being spaced apart from adjacent heating unit and mounted on an upper surface of the first substrate;
    a PCR chip including:
        a second substrate having a flat-plate shape, and
        reaction chambers spaced apart from each other and mounted on an upper surface of the second substrate,
    wherein the PCR chip is configured to slide in a unidirectional manner on the PCR thermal block while maintaining a contact between the second substrate of the PCR chip and the plurality of heating units mounted on the upper surface of the first substrate of the PCR thermal block in a state where the PCR chip is mounted on the PCR thermal block,
    wherein the first and second heaters of each of the plurality of heating units are spaced apart from each other along a sliding direction,
    wherein the reaction chambers each in the PCR chip are spaced apart along the sliding direction,
    wherein each of the reaction chambers in the PCR chip is configured to have a sequential thermal contact from a heater of the plurality of heating units mounted at one end of the PCR thermal block to a heater of the plurality of heating units mounted at another end of the PCR thermal block,
    wherein the reaction chambers are repeatedly arranged in the PCR chip in a manner that each of the reaction chambers sequentially and independently meets each heater of each heating unit in the PCR thermal block in response to the sliding of the PCR chip relative to the PCR thermal block, and
    wherein the PCR device further comprises:
        a plurality of light sources for supplying light to the reaction chambers of the PCR chip, each light source being positioned on the PCR thermal block between the first and second heaters of each of the plurality of heating units of the PCR thermal block and spaced apart along the sliding direction; and
        at least one light detector for detecting optical signals generated from the reaction chambers of the PCR chip,
    wherein the reaction chambers of the PCR chip are arranged to correspond to the heating units of the PCR thermal block, and the light sources of the PCR thermal block are arranged to correspond to the reaction chambers of the PCR chip,
    wherein the light sources are configured to be arranged to vertically correspond to the reaction chambers with respect to the sliding direction, such that the at least one light detector detects the optical signals generated from the reaction chambers by the light emitted from the light sources arranged to vertically correspond to the reaction chambers, and
    wherein the at least one light detector is positioned above the PCR chip and configured to move corresponding to a movement route of the PCR chip.

2. The PCR device according to claim 1, wherein each heating unit in the PCR thermal block having the first heater and the second heater is repeatedly mounted on the upper surface of the first substrate along the sliding direction.

3. The PCR device according to claim 2, wherein the first heater has a temperature of 85° C. to 105° C. and the second heater has a temperature of 50° C. to 80° C.

4. The PCR device according to claim 3, wherein the first heater has a temperature of around 95° C. and the second heater has a temperature of around 72° C.

5. The PCR device according to claim 1, wherein the second substrate of the PCR chip is bonded or attached to the PCR thermal block, transfers heat from the PCR thermal block to the reaction chambers, and is made of a material selected from the group consisting of polydimethylsiloxane (PDMS), cyclo-olefin copolymer (COC), polymethylmethacrylate (PMMA), polycarbonate (PC), polypropylene carbonate (PPC), polyether sulfone (PES), polyethylene terephthalate (PET), and a combination thereof.

6. The PCR device according to claim 1, wherein a PCR carried out in a reaction chamber of the reaction chambers of the PCR chip initiates when the reaction chamber is in thermal contact with a heater of the plurality of heating units at the one end of the PCR thermal block and terminates when the reaction chamber is in thermal contact with a heater of the plurality of heating units located at the another end of the PCR thermal block.

7. The PCR device according to claim 1, wherein each of the reaction chambers in the PCR chip is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof.

8. The PCR device according to claim 1, wherein each of the reaction chambers in the PCR chip has a width of 0.001 mm to 10 mm and a length of 1 mm to 400 mm.

9. The PCR device according to claim 1, wherein the reaction chambers in the PCR chip are formed in a channel type.

10. The PCR device according to claim 1, wherein the respective reaction chambers of the PCR chip further include an integrated inlet/outlet well.

11. The PCR device according to claim 1, wherein the respective reaction chambers of the PCR chip further include an inlet, an outlet, and a single channel connecting the inlet and the outlet.

12. The PCR device according to claim 1, wherein the light detector moves in correspondence to a movement of the PCR chip.

13. The PCR device according to claim 1, wherein the second substrate and the reaction chambers of the PCR chip are made of a transmissive material.

14. The PCR device according to claim 1, wherein the PCR chip further comprises a detection electrode for detecting electrochemical signals generated by combining amplified nucleic acids from a PCR to a redox indicator in the reaction chambers.

15. The PCR device according to claim 14, further comprising an electrochemical signal measuring circuit electrically connected to the detection electrode to measure said electrochemical signals generated in the reaction chambers of the PCR chip.

16. The PCR device according to claim 1, wherein the PCR chip further comprises:
   an immobilization layer formed on one region of an interior of the reaction chambers and subjected to surface treatment with a capture probe capable of being complementarily bonded to one region of amplified nucleic acids from a PCR;
   a detection electrode formed on other region of the interior of the reaction chambers for detecting electrochemical signals generated by combining the amplified nucleic acids to a redox indicator; and
   composites having metal nanoparticles and signaling probes connected to the metal nanoparticles being complementarily bonded to other region of the amplified nucleic acid.

17. The PCR device according to claim 16, further comprising an electrochemical signal measuring circuit electrically connected to the detection electrode to measure said electrochemical signals generated in the reaction chamber of the PCR chip.

18. The PCR device according to claim 1, further comprising a chip standby part comprising a plurality of PCR chips.

19. The PCR device according to claim 18, wherein each of the plurality of PCR chips in the chip standby part is configured to sequentially slide relative to the PCR thermal block.

* * * * *